US008597616B2

(12) United States Patent
Kraft et al.

(10) Patent No.: US 8,597,616 B2
(45) Date of Patent: Dec. 3, 2013

(54) DRY POWDER DRUG DELIVERY FORMULATIONS, METHODS OF USE, AND DEVICES THEREFORE

(75) Inventors: Edward R. Kraft, Galveston, TX (US); Stephen L. Hoskins, Galveston, TX (US); Perenlei Enkhbaatar, Galveston, TX (US); Daniel L. Traber, Galveston, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 1024 days.

(21) Appl. No.: 12/256,438

(22) Filed: Oct. 22, 2008

(65) Prior Publication Data

US 2012/0111324 A1 May 10, 2012

Related U.S. Application Data

(60) Provisional application No. 60/981,630, filed on Oct. 22, 2007.

(51) Int. Cl.
*A61K 31/137* (2006.01)
*A61K 9/72* (2006.01)
*A61M 15/00* (2006.01)

(52) U.S. Cl.
USPC .............................. 424/46; 424/489; 514/653

(58) Field of Classification Search
None
See application file for complete search history.

(56) References Cited

U.S. PATENT DOCUMENTS

| | | | |
|---|---|---|---|
| 3,095,355 A | 6/1963 | Abramson | |
| 3,219,533 A * | 11/1965 | Mullins | 222/192 |
| 3,809,084 A * | 5/1974 | Hansen | 128/203.15 |
| 5,156,776 A | 10/1992 | Loedding et al. | |
| 5,438,982 A | 8/1995 | MacIntyre | |
| 5,642,730 A | 7/1997 | Baran | |
| 5,676,929 A | 10/1997 | Akehurst et al. | |
| 5,752,663 A | 5/1998 | Fischer et al. | |
| 5,801,294 A * | 9/1998 | Sage et al. | 570/177 |
| 5,868,322 A | 2/1999 | Loucks, Jr. et al. | |
| 5,964,223 A | 10/1999 | Baran | |
| 6,032,876 A | 3/2000 | Bertsch et al. | |
| 6,079,413 A | 6/2000 | Baran | |
| 6,224,885 B1 | 5/2001 | Jenner et al. | |
| 6,375,962 B2 | 4/2002 | Jenner et al. | |
| 6,455,751 B1 | 9/2002 | Hoffman et al. | |
| 6,526,976 B1 | 3/2003 | Baran | |
| 6,729,334 B1 | 5/2004 | Baran | |
| 6,787,104 B1 | 9/2004 | Mariella, Jr. | |
| 6,977,171 B1 | 12/2005 | Dennis et al. | |
| 7,087,805 B2 | 8/2006 | Centanni et al. | |
| 7,186,375 B2 | 3/2007 | Centanni et al. | |
| 7,279,129 B2 | 10/2007 | Lanz et al. | |
| 7,354,429 B2 | 4/2008 | Sparks et al. | |
| 7,445,799 B1 | 11/2008 | Sarangapani et al. | |
| 7,947,742 B2 | 5/2011 | Batycky et al. | |
| 2003/0234015 A1 * | 12/2003 | Bruce et al. | 128/200.23 |
| 2004/0076588 A1 * | 4/2004 | Batycky et al. | 424/46 |
| 2004/0191176 A1 | 9/2004 | Kaplan | |
| 2005/0121025 A1 | 6/2005 | Gamard et al. | |

FOREIGN PATENT DOCUMENTS

WO 9917754 A1 4/1999
WO 2007123945 11/2007

OTHER PUBLICATIONS

"A vote for inhaled adrenaline in the treatment of severe upper airway obstruction caused by piercing of the tongue in hereditary angioedema" by Trachsel et al., J. Intensive Care Med. 25, 1135-36 (1999).*
International Search Report for International Patent Application No. PCT/US2008/080811, European Patent Office, dated Jun. 25, 2009.
Written Opinion for International Patent Application No. PCT/US2008/080811, European Patent Office, dated Jun. 25, 2009.
Ellen Moyse, International Preliminary Report on Patentability, The International Bureau of WIPO, Switzerland, dated Apr. 27, 2010.
Wang, Jianpu; Zhang, Liming; and Walther, Sten M., "Inhaled Budesonide in Experimental Chlorine Gas Lung Injury: Influence of Time Interval Between Injury and Treatment", Intensive Care Medicine, vol. 28 (No. 3), pp. 352-357 (2002).
Wang, J.; Winskog, C.; Edston, E., and Walther, S.M., "Inhaled and Intravenous Corticosteroids Both Attenuate Chlorine Gas-Induced Lung Injury in Pigs", Acta Anaesthesiol. Scand., vol. 49, pp. 183-190 (2005).
Wang, Jianpu and Walther, Sten M., "Chlorine Gas Inhalation: Mechanisms of Injury and Treatment", International Journal of Disaster Medicine, vol. 2, pp. 75-81 (2004).
Zanen, Pieter; Go, Liam T., and Lammers, Jan-Willem, "The Optimal Particle Size for Parasympathicolytic Aerosols in Mild Asthmatics", International Journal of Pharmaceutics, vol. 114 (Issue 1), pp. 111-115 (1995).
Wang, Jianpu; Zhang, Liming; and Walther, Sten M., "Administration of Aerosolized Terbutaline and Bedesonide Reduces Chlorine Gas-Induced Acute Lung Injury", The Journal of Trauma, Injury, Infection and Critical Care, vol. 56, pp. 850-862 (2004).
"Prevention and Treatment of Injury from Chemical Warfare Agents", in The Medical Letter on Drugs and Therapeutics, vol. 44 (No. 1), pp. 1-10 (Jan. 7, 2002).
Ventolin HFW Product Information, GlaxoWellcome, Dec. 22, 2000.

(Continued)

*Primary Examiner* — Anna Pagonakis
*Assistant Examiner* — Theodore R West
(74) *Attorney, Agent, or Firm* — Wong, Cabello, Lutsch, Rutherford & Brucculeri, LLP.

(57) ABSTRACT

The present disclosure relates to systems, methods, and formulations for the pulmonary administration of one or more therapeutic agents, in dry powder form, in a single, large dose quantity. These formulations, methods, and systems are useful in the treatment of patients suffering from toxic or harmful gas exposure, such as nerve gas exposure, as well as in the treatment of patients suffering from diseases of the pulmonary system, including tuberculosis, cystic fibrosis, and chronic obstructive pulmonary disease (COPD).

10 Claims, 6 Drawing Sheets

(56) References Cited

OTHER PUBLICATIONS

Primatene Mist Product Information, Armstrong Pharmaceuticals, Marketing Approval 1984.
CDC NIOSH Pocket Guide to Chemical Hazards: dichlorotetrafluoroethane. Aug. 21, 2012.
CDC NIOSH Pocket Guide to Chemical Hazards: dichlorodifluormethane. Aug. 21, 2012.
Dupont Freon 114 MSDS: Jan. 1, 1997.
CDC NIOSH Pocket Guide to Chemical Hazards: 1,1,1,2-tetrafluoroethane. Oct. 12, 2012.

* cited by examiner

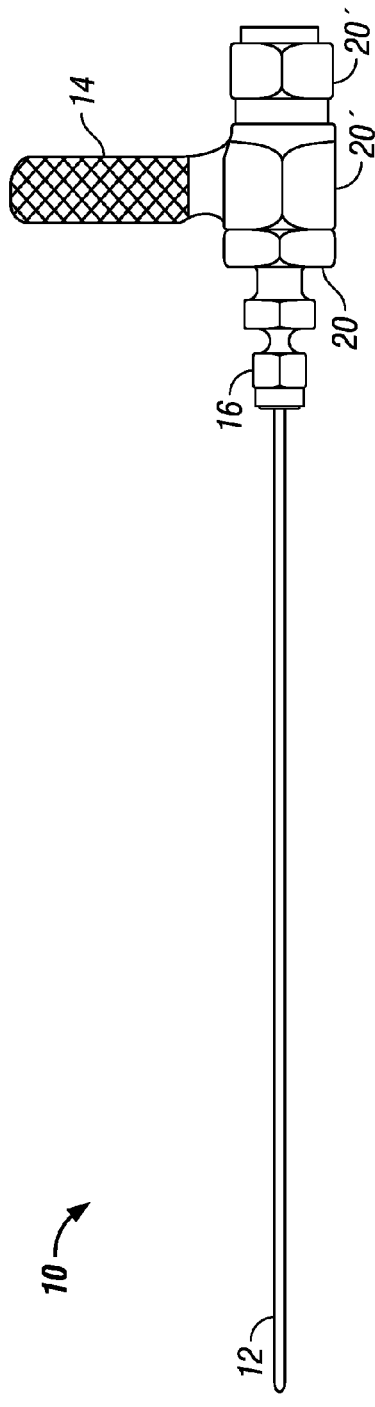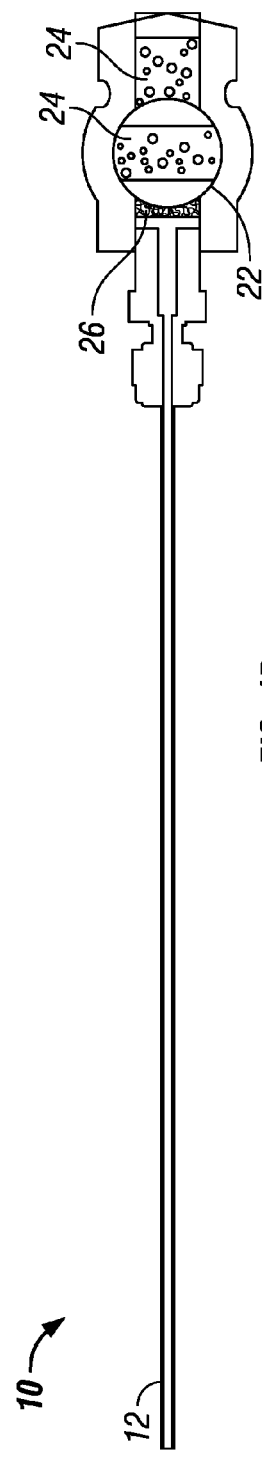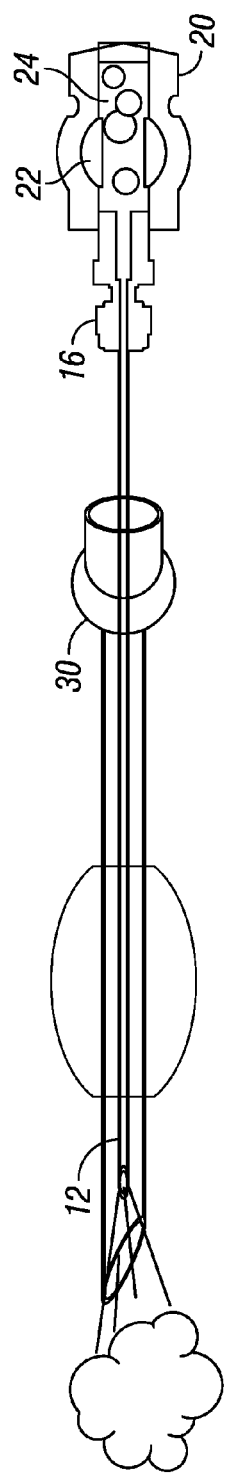

DRY POWDER DRUG DELIVERY FORMULATIONS, METHODS OF USE, AND DEVICES THEREFORE

CROSS REFERENCE TO RELATED APPLICATIONS

The present application claims priority to U.S. Provisional Patent Application Ser. No. 60/981,630, filed Oct. 22, 2007, the contents of all of which are incorporated herein by reference.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

1. Field of the Invention

This disclosure relates generally to systems and methods for the delivery of dry powder compositions of therapeutic agents to a patient, and more particularly, to systems, methods, and compositions for the pulmonary delivery of large doses of dry powder compositions of therapeutic agents to a patient in a single application.

2. Description of the Related Art

There are numerous emergency situations where individuals are exposed to one or more toxic agents via inhalation, wherein failure to rapidly provide treatment protocols can lead to debilitating complications and in many cases, death. These situations include not only the exposure of individuals to nuclear, biological, or chemical (NBC) agents in industrial settings, such as when accidents occur in the industrial setting or during chemical transport, but also the exposure of individuals to such agents during warfare or terrorist events. Often, in order to attempt to counter-act the exposure, large doses of drugs must be administered in a rapid manner in order to begin their therapeutic introduction into the patient's systemic circulation. For example, exposure to Sarin, Suman, Tabun, Vx, any number of toxic organophosphates (OPs), or other chemical warfare agents demands the immediate administration of antidote or antidote combination in order to ameliorate the debilitating effects on the battlefield and prevent death. For example, in the event of exposure to Sarin or related, toxic compounds, reversal of nerve agent toxicity depends on the prompt, parenteral administration of the antidotes, such as atropine and pralidoxime (2-PAM-CL), alone or in combination, often in multiple doses over a short period of time.

Although the intravenous (IV) administration of these antidotes has previously and often been preferred, this is not practical in combat situations or civilian mass casualty incidents. In the military, these drugs are typically self-administered intramuscularly (such as in the outer thigh muscle or other large muscle area) with devices such as the Mark I auto-injector, a disposable, spring-loaded and pressure-activated system preloaded with mediation (AtroPen® and ComboPen®). Previous studies have suggested that an intramuscular (IM) injection of 2-PAM-CL (pralidoxime) takes about 2 minutes to reach therapeutic levels in a normovolemic swine model. Peak blood levels of 2-PAM-CL were reached at 8 minutes post-injection. In the instances described herein, time is a critical factor in treatment for nerve agent or toxic chemical exposure, and the reduction in time of delivering a drug to the systemic circulation may save lives.

Inhaled drug delivery is an effective method to introduce drugs into the lungs, pulmonary region, and systemic circulation system of a patient. Inhaled drug delivery is a proven modality for both lung diseases as well as fast acting medicines than cannot be absorbed via the gastro-intestinal tract or when vascular access is not an option due to time limitations or circulatory collapse. The large surface area of the lung is in immediate proximity to the circulating blood supply and can provide a very large permeable surface through which some drugs can quickly pass into the circulating blood.

Deposition into the deep lung (parenchyma distal to the bronchi) has been established to be greatly size dependent. In general, aerosols or particles in the 1-5 µm diameter range will deposit into the distal lung parenchyma were oxygen transport occurs. Dry powder drug particles can be easily and consistently manufactured in the 0.5-5 µm diameter range so that they are suitable for pulmonary delivery and may deposit in the lung parenchyma for systemic or local absorption. This technology exists and is in use for administration of small dose bronchodilators, anti-inflammatories, and insulin.

Nerve agent exposure, toxic chemical exposure, or cardiac collapse are critical situations were it would be advantageous to deliver large dosages of drugs into a patient. Existing emergency drug delivery, when establishment of intravenous access is not an option, is currently performed with an intramuscular auto-injector for NBC exposure or, intraosseous administration (injection or infusion directly into the marrow of a bone, such as the tibia, via a cannula or the equivalent), or endotracheal for the treatment of cardiac arrest. The intramuscular route is relatively slow (2-3 minutes) in delivering protective blood levels of the drug. The intraosseous route has a faster circulatory absorption rate than intramuscular delivery once established but the administration is painful, expensive, requires critical training to use, and is not a realistic option for self administration. In addition, both autoinjector and intraosseous administration require individuals to overcome the anxiety of self injection which may cost valuable time measured in seconds till the drug is administered. Inhaled nebulized liquid or dry powder is particularly useful for delivering bronchodilators for treatment of acute asthmatic symptoms. In this instance, relatively small doses of drugs can be administered via inhalation to effectively and quickly treat broncospasm and restore normal breathing. However, the total drug payload per breath in existing nebulized liquid or dry powder "inhaler" type devices is relatively small.

Existing nebulized liquid has limitations of total drug payload that can be effectively introduced into the inspired air flow. Large volumes of liquefied gas are required to nebulize small quantities of a liquid drug suspension into droplets suitable for pulmonary drug delivery. In this case, most of the inhaled breath volume is the result of the expanded gas from the liquid propellant with very little actual drug volume suspended in that gas volume. The relatively small drug payload per breath would make this system inappropriate for large dosage emergency drug administration, such as in the instance of a person's exposure to a hazardous chemical or other toxic gas agent.

Existing dry powder pulmonary drug delivery technology approaches rely on the active inspiration of the subject to provide enough air velocity over a dry powder reservoir to disperse and suspend the powder from the reservoir into the inspired air flow. In general, the total maximum drug dosage that can be suspended and delivered by these currently existing methods is less than about 0.5 milligram per breath of the patient. Again, the relatively small drug payload per breath would make this system inappropriate for large dosage drug administration in an emergency situation.

This application for patent discloses systems, methods, and therapeutic compositions and formulations for the large-scale, dry powder endotracheal delivery of therapeutic agents to a patient suffering a pulmonary inflammatory response to an external agent.

BRIEF SUMMARY OF THE INVENTION

In accordance with a first aspect of the present disclosure, systems for the endotracheal administration of dry powder therapeutic agents into the lung of a patient by insufflation using a liquefied gas propellant to suspend and then release and disperse the therapeutic agent into an inhalable gas prior to administration are described.

In further aspects of the present disclosure, devices are described wherein therapeutic agents, in the form of dry powder, are suspended in a pressurized liquefied gas housed in a first chamber so as to form a gas/dry powder suspension, wherein the chamber is configured for the release of the liquefied gas/dry powder causing the dry powder to be suspended in the gas phase of the suspension; and wherein the dry powder/gas suspension is made available for insufflation into the lungs of a mammal.

Devices wherein medicines, in the form of dry powder, are in a reservoir adjacent to a pressurized liquefied gas housed in a chamber; wherein the chamber is configured to release the liquefied gas causing the dry powder to be suspended in the gas phase of the liquefied gas; wherein the dry powder/gas suspension is made available for insufflation into the lungs of a mammal.

In accordance with further aspects of the present disclosure, a system comprising a micronized drug powder suspended in a liquefied gas that is released into the pulmonary system of a mammal causing the drug to be disbursed into the lung and then absorbed into the circulating blood or lung tissues is described. Advantageously, such systems can allow for several dry powder compounds to be co-mingled or admixed in the inert environment of the propellant, such that they will not react with each other in the absence of air and water. This may in turn aid in prolonging the shelf life of the systems and formulations contained therein, and extend the system's usage extremes (e.g., allowing the systems and the formulations contained therein to be more resistant to fluctuations in pressure, heat/temperature, and/or moisture).

In according to further aspects of the present disclosure, methods for the delivery of one or more therapeutic agents in dry powder form to the lungs of a patient, for use in therapeutically treating pulmonary disorders, including tuberculosis (TB), cystic fibrosis (CF), or toxic gas inhalation (such as chlorine, bromine, phosgene, or one or more nerve agents of the V- or G-series) are also described.

In accordance with yet another aspect of the present disclosure, a method for the treatment of a pulmonary disorder, endotracheal event, bronchospasm, or for providing a rescue medication is described, wherein the method comprises administering to a patient in need of such treatment or medication, a medicament comprising epinephrine or an analogue thereof. In accordance with this aspect, the medicament is a dry powder composition for pulmonary delivery, comprising microparticles of epinephrine, wherein the microparticles have a mean mass aerodynamic diameter of less than 10 µm, and optionally a MMAD of less than about 5 µm.

In yet another aspect of the present disclosure, a dry powder aerosol pharmaceutical formulation is described, the formulation comprising at least one adrenergic agonist as active ingredient in a dosage amount of at least 20 mg, wherein the at least one adrenergic agonist active ingredient is milled to an average particle size of less than about 10 µm. In accordance with further embodiments of this aspect of the present disclosure, the adrenergic agonist is milled to an average particle size of less than about 5 µm. In still further accordance with this aspect, the adrenergic agonist is epinephrine or an analog thereof.

In further aspects of the present disclosure, devices adapted to contain and disperse dry powder drug formulations as detailed herein are described, wherein such devices preferably use or are based on the use of non-CFC liquefied propellants to deliver the dry powder therapeutic formulations to the target pulmonary region of a patient. In accordance with this aspect of the disclosure, a metered dose dry powder aerosol inhaler comprising a dry powder formulation of the present disclosure and a haloalkane propellant are described, wherein the haloalkane propellant is 1,1,2,2-tetrafluoroethane (R-134a).

In further aspects of the present disclosure, a bioactive, spray-dried powder composition for pulmonary delivery is described, the composition comprising (i) a therapeutically effective amount of an adrenergic agonist; (ii) a pharmaceutically acceptable carrier; and optionally (iii) a haloalkane propellant, wherein the composition is substantially free from penetration enhancers. In accordance with this aspect of the disclosure, a method for preparing bioactive, spray-dried, adrenergic agonist-based dry powder compositions are described, the methods comprising spray-drying a gaseous solution of an adrenergic agonist and a carrier, under conditions to provide a respirable dry powder, which, when administered pulmonarily in association with a propellant, is rapidly systemically absorbed by a patient. In further accordance with these aspects of the disclosure, a method for aerosolizing a spray-dried, bioactive epinephrine-based dry powder composition is described, the method comprising dispersing an amount of a dry powder composition as described herein in a gas stream comprising a haloalkane propellant to form an aerosol, and capturing the aerosol in a chamber of a delivery device for subsequent inhalation by a patient.

The therapeutic agents suitable for use herein may include but are not limited to epinephrine, pralidoxime chloride, atropine, antihistamines, anti-inflammatories, antibiotics, steroids, NSAIDs, $\beta_2AR$ agonists, antioxidants, insulin, and combinations thereof.

BRIEF DESCRIPTION OF THE SEVERAL VIEWS OF THE DRAWINGS

The following figures form part of the present specification and are included to further demonstrate certain aspects of the present invention. The invention may be better understood by reference to one or more of these figures in combination with the detailed description of specific embodiments presented herein.

FIG. 1A illustrates a perspective view of an exemplary experimental system for actuated dry powder administration, in accordance with aspects of the present disclosure.

FIG. 1B illustrates a cross-sectional view of the system of FIG. 1A.

FIG. 1C illustrates the cross-sectional view of the system of FIG. 1B with the ball valve rotated.

Figure 1D:
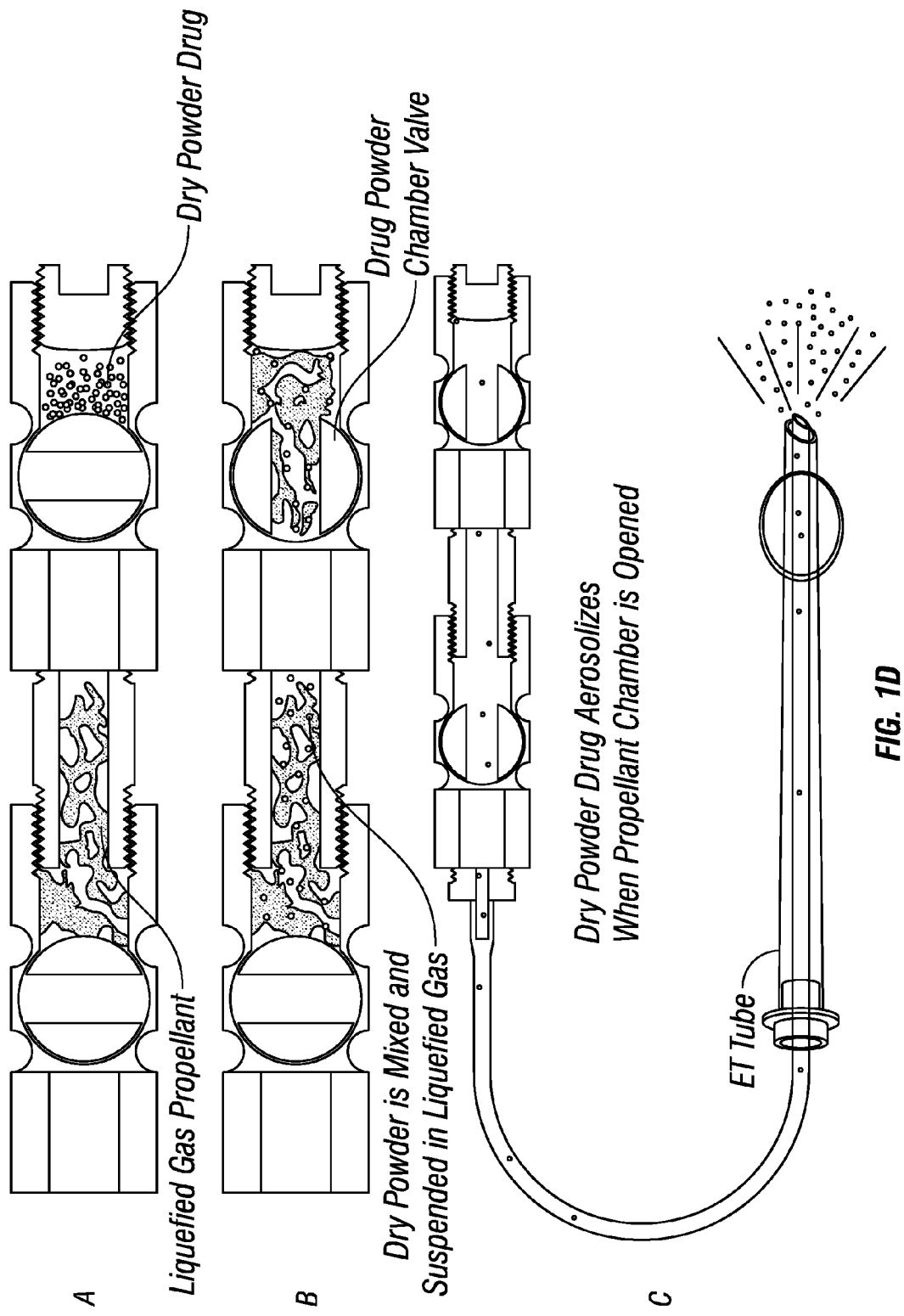
FIG. 1D illustrates a further exemplary experimental setup and method of use for an exemplary actuated dry powder delivery system of the present disclosure.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

DEFINITIONS

The following definitions are provided in order to aid those skilled in the art in understanding the detailed description of the present invention.

The phrase "pharmaceutical composition" refers to a formulation of a compound and a medium generally accepted in the art for the delivery of the biologically active compound to mammals, e.g., humans. Such a medium includes all pharmaceutically acceptable carriers, diluents or excipients therefore.

The phrase "pharmaceutically acceptable carrier, diluent or excipient" as used herein includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The term "powder", as used herein, means a composition that consists of finely dispersed solid particles that are free-flowing and capable of being readily dispersed in an inhalation device and subsequently inhaled by a subject, so that the particles reach the lungs so as to permit penetration into the alveoli. Thus, the powder is said to be "respirable." Preferably, in accordance with the present disclosure, the average particle size of the powder is less than about 10 microns (μm) in diameter, with a relatively uniform, spheroidal shape distribution. Typically, the particle size distribution is between about 0.1 μm and about 5 μm in diameter, more particularly from about 2 μm to about 5 μm.

The term "dry", as used herein, means that the composition has a moisture content such that the particles are readily dispersible in an inhalation device so as to form an aerosol. In accordance with the present disclosure, this moisture content is preferably less than about 10 weight percent (wt. %) water, typically less than about 5 wt. %, and preferably less than about 4 wt. %.

The term "therapeutically effective amount", as used herein, the dose administered to an animal, such as a mammal, in particular a human, should be sufficient to prevent the targeted disease or disorder, e.g., cancer, delay its onset, slow its progression, or treat the disease or disorder (e.g., reverse or negate the condition). One skilled in the art will recognize that dosage will depend upon a variety of factors including the strength of the particular composition employed, as well as the age, species, condition, and body weight of the animal. The size of the dose will also be determined by the route, timing, and frequency of administration as well as the existence, nature, and extent of any adverse side-effects that might accompany the administration of a particular composition and the desired physiological effect.

"Biological active agent", as used herein, refers to any amino acid, peptide, protein, or antibody, natural or synthetic, which exhibits a therapeutically useful effect. Such biologically active agents may include recombinant proteins, enzymes, peptoids, or PNAs, as well as combinations of such agents.

The phrase "pharmaceutically acceptable" or "pharmacologically-acceptable" refers to compositions that do not produce an allergic or similar unexpected reaction when administered to a human or animal in a medical or veterinary setting.

The compositions of the present invention may be prepared for pharmaceutical administration by methods and with excipients generally known in the art, such as described in *Remington's Pharmaceutical Sciences* [Troy, David B., Ed.; Lippincott, Williams and Wilkins; 21st Edition, (2005)].

"Treating" or "treatment" as used herein covers the treatment of the disease or condition of interest, e.g., tissue injury, in a mammal, preferably a human, having the disease or condition of interest, and includes: (i) preventing the disease or condition from occurring in a mammal, in particular, when such mammal is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition.

As used herein, the terms "disease," "disorder," and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The term "water-insoluble" encompasses the terms sparingly water-soluble, slightly or very slightly water-soluble, as well as practically or totally water-insoluble compounds [see, *Remington: The Science and Practice of Pharmacy*, vol. 1, 194-195 (Gennaro, ed., 1995)]. As used herein, a compound is water-insoluble for the purposes of this invention if it requires at least 30 parts solvent (e.g., water or saline) to dissolve one part solute (Id.). In accordance with the present disclosure, the term "water-insoluble" also encompasses oil- or lipid-soluble, as well as substantially oil- or lipid soluble.

Except as otherwise specifically provided or clear from the context, the term "compounds" of the invention should be construed as including the "pharmaceutically acceptable salts" thereof (which expression has been eliminated in certain instances for the sake of brevity).

As used herein, the term "%" when used without qualification (as with w/v, v/v, or w/w) means % weight-in-volume for solutions of solids in liquids (w/v), % weight-in-volume for solutions of gases in liquids (w/v), % volume-in-volume for solutions of liquids in liquids (v/v) and weight-in-weight for mixtures of solids and semisolids (w/w), such as described in *Remington's Pharmaceutical Sciences* [Troy, David B., Ed.; Lippincott, Williams and Wilkins; 21st Edition, (2005)].

The terms "patient" and "subject", as used herein, are used interchangeably and refer generally to a mammal, and more particularly to human, ape, monkey, rat, pig, dog, rabbit, cat, cow, horse, mouse, sheep and goat. In accordance with this definition, lung surfaces or membranes described and referenced in accordance with this disclosure refer to those of a mammal, preferably a human or an animal test subject, such as a sheep.

The term "particle size" or "droplet size" is used in the context of the present disclosure to refer to the average diameter of particles, e.g., drug, lipid vesicles, in a suspension, and is defined herein as the "Mass Median Aerodynamic Diameter" (MMAD) which is referenced from an equivalent aqueous solution with a density of 1.0 g/ml. As the fluid density decreases the real droplet diameter/volume increases and conversely. Generally speaking, lung deposition of a particle or droplet is primarily dependent on the MMAD of the individual particle or droplet.

The term "spray dry" refers to a nebulization method that allows for the evaporation of a solvent in part of the nebulized formulation that results in a smaller droplet after a time when a portion of the droplet has evaporated. Within the context of this disclosure spray drying is an essential part of the operation of handheld inhalers as well as the operation of pharmaceutical manufacturing methods and column injection in analytical chemistry application especially in gas chromatography.

The term "droplet" (or a tiny drop) is an individual particle from a fine spray of liquid that was nebulized into an aerosol.

"Insufflation" as used herein refers to blowing or inhaling a medicinal powder, solution or formulation into the lungs of a patient.

The term "hygroscopic" generally refers herein to a condition whereby a nebulized droplet composition absorbs water from the humidity in the droplet air stream and causes the droplet to expand and grow causing the MMAD to increase in size.

The term "drug" as used in conjunction with the present disclosure means any compound which is biologically active, e.g., exhibits or is capable of exhibiting a therapeutic or prophylactic effect in vivo, or a biological effect in vitro.

The term "controlled drug-delivery system", or "DDS", as used herein, refers to a formulation that controls the rate and period of therapeutic agent/drug delivery (i.e., time-release dosage), targets specific areas of the subjects body, and are designed to maintain therapeutic levels during the desired treatment period, such as described by M. Vallet-Regi [*Chem. Eur. J.*, Vol. 12, pp. 5934-5943 (2006)].

As used herein, the term "epinephrine" refers to (R)-4-(1-hydroxy-2-(methylamino)ethyl)benzene-1,2-diol, having CAS registry number 51-43-4, as well as derivatives thereof and their pharmaceutically acceptable salts, solvates, hydrates, prodrugs, and polymorphs thereof.

The term "$\beta_2$-adrenoceptor agonist", or equivalently "$\beta_2$AR agonist", as used herein, refers to therapeutic agents or combinations of agents which act on the $\beta_2$ adrenoceptors of bronchial muscle.

The term "steroid", as used herein, refers to those therapeutic compounds, both synthetic and naturally-occurring, that are capable of binding to one or more steroid hormone receptors, and having the general chemical skeleton (a tetracyclic cyclopenta[a]phenanthrene skeleton core structure) shown below.

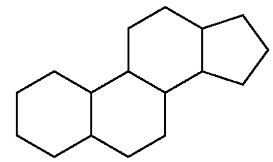 [SMILES: C1CCC2C(C1)CCC1C3CCCC3CCC21]

The term "antioxidant", as used herein, refers to those substances that are capable of reducing oxidative damage (damage due to oxygen), such as that caused by free radicals (highly reactive chemicals that attack molecules by capturing electrons and thus modifying chemical structures). Exemplary antioxidants include enzymes, vitamins, and their derivatives.

"Nerve agent", also equivalently referred to as "nerve gases", as used herein, refers to the class of phosphorus-containing organic chemicals (organophosphates) that are capable of disrupting the mechanism by which nerves transfer messages to the organs. This disruption may be caused by blocking acetylcholinesterase, an enzyme that normally relaxes the activity of acetylcholine, a neurotransmitter, as well as by other mechanisms of action.

As used herein, the term "OP" refers to organophosphorus compounds, in particular those phosphorous containing compounds and agents which act primarily by inhibiting acetylcholinesterase, such as a number of commercially-available insecticides and pesticides.

The term "G-series nerve agent", as used herein, refers to the organophosphate nerve agents tabun (GA), sarin (GB), soman (GD), and cyclosarin (GF).

The term "V-series nerve agent", as used herein, refers to the most highly toxic chemical warfare nerve agents, having the capacity to inactivate the enzyme acetylcholinesterase (AChE), and being also classified as a part of the group of persistent agents, which are nerve agents that can remain on skin, clothes, and other surfaces for long periods of time. The V-series of nerve agents includes O-ethyl S-(2-diisopropylamino ethyl)methylphosphonothioate (VX), O-Ethyl-S-[2-(diethylamino)ethyl]ethylphosphonothioate (VE), the Russian equivalent of VX (V-gas), O,O-Diethyl-S-[2-(diethylamino)ethyl]phosphorothioate (VG), and O-Ethyl-S-[2-(diethylamino)ethyl]methylphosphonothioate (VM).

The term "binary nerve agent", as used herein, refers to a projectile or other nerve agent delivery system that contains at least 2 separate, hermetically sealed, plastic-lined containers fitted, one behind the other, in the body of the projectile or delivery system, including but not limited to GB2, GD2, and VX2. In the GB2 binary weapon, the forward canister contains methylphosphonic difluoride (DF), and the rear canister contains an isopropyl alcohol and isopropylamine solution (OPA); in the GD2 binary weapon, DF is located in 1 canister, while a mixture of pinacolyl alcohol and an amine is in a second canister, such that after deployment of the weapon, the 2 canisters rupture and the chemical mixture produces GD; and, in the VX binary system (VX2), O-Ethyl O-2-diisopropylaminoethyl methylphosphonite (QL) is in 1 canister, and the other canister contains elemental sulfur—when the weapon is fired, the canisters rupture and the chemical mixture produces VX.

DETAILED DESCRIPTION

One or more illustrative embodiments incorporating the invention disclosed herein are presented below. Not all features of an actual implementation are described or shown in this application for the sake of clarity. It is understood that in the development of an actual embodiment incorporating the present invention, numerous implementation-specific decisions must be made to achieve the developer's goals, such as compliance with system-related, business-related, government-related and other constraints, which vary by implementation and from time to time. While a developer's efforts might be complex and time-consuming, such efforts would be, nevertheless, a routine undertaking for those of ordinary skill the art having benefit of this disclosure.

In general terms, Applicants have created a nebulizer systems suitable for the one-time delivery of a large quantity of a pulmonary-directed dry-powder therapeutic agent or combination of such agents, particularly useful in emergency and life-threatening situations, as well as methods and formulations related to the use of such systems in therapeutic administration of therapeutic agents in dry powder form.

The present disclosure also provides methods and compositions therein for stimulating cardiovascular and/or respiratory output in a human patient during situations wherein the patient has come into contact with a nerve agent, or toxic chemical agent, particularly wherein the agent contacting the patient is in high concentrations and is in at least partially-gaseous form. Such situations may be encountered by emergency personnel, soldiers in military combat, and others during terrorist attacks, during warfare, and in the case of industrial accidents, such as chemical spills. In accordance with certain aspects of the present disclosure, the administration of dry powder formulations of adrenergic agonists such as epinephrine in dosage amounts greater than about 20 mg/dose have been found to provide beneficial, and potentially life-saving, effects.

Also described herein, Applicants have developed a pulmonary drug delivery system whereby large drug dosages, in a dry drug powder form, can be suspended into an inhaled air steam, such as in a respiratory therapeutic delivery device, for pulmonary deposition to a patient, and subsequent circulatory blood absorption of the therapeutic agent. The system is small, lighter than existing auto-injectors kits, and activated in a few seconds. This system could be used to deliver nerve agent antidotes such as Pralidoxime chloride (2-PAM-Cl) and atropine to the systemic circulation within seconds. In addition, the system could easily be adapted for administration of large dose steroids and bronchodilators for toxic chemical exposure.

The currently disclosed and described system has several advantages over existing technology. In accordance with aspects of the disclosure, we utilize a propellant, such as R-134a (1,1,1,2-tetrafluoroethane, a haloalkane refrigerant without an ozone depletion potential and thermodynamic properties similar to R-12 (dichlorodifluoromethane)), to disperse the drug into an inspirable air volume which dramatically increases drug payload over that which can be delivered by common inhalers. Secondly, the micronization of the drug enables the currently-described system to effectively deliver large amounts (greater than 50 or 100 mg) of therapeutic agents to the highly vascularized areas of the deep lung of a patient, thereby increasing drug absorption. This, in turn, equates to faster drug delivery into to the systemic circulation of the patient. In preliminary studies using our system we evaluated epinephrine delivery in the compromised circulation (during CPR) using a swine model. A rapid and sustained MAP occurred in <60 seconds using the dry powder drug delivery system. This was similar to the effects seen when epinephrine was delivered by the central venous route. Therapeutic agents, in the form of an inhalable micronized dry powder, offers superior drug delivery parameters with administration ease and very rapid drug absorption into the blood.

The actuated dry powder pulmonary drug delivery system (DPET) disclosed herein allows large doses of micronized drugs (>20 milligrams) to be suspended into an inspired air stream and inhaled for deep lung deposition. In this system, drug powder (milled to a size ranging from, for example, about 0.5 µm to about 5 µm in size) is suspended in a small quantity of liquefied gas propellant tetraflourethane (R-134a, a common propellant for inhaled medicines) within a small (1.5 cc) pressurized chamber. When the chamber is opened, the liquefied propellant containing the drug expands into a gas phase dispersing and suspending the micronized dry powder into the inspirable gas and then into the deep lung.

This novel method of delivering large dosage of dry powder via the pulmonary route significantly improves treatment in emergent situations as the drugs are absorbed into the systemic circulation faster than drugs delivered by the intramuscular route. Emergency drug administration for nerve agent countermeasures is currently performed using an intramuscular injection delivered by an autoinjector. IM drug delivery of 2-PAM-Cl takes between 2-3 min to reach therapeutic levels in the systemic circulation (unpublished data). The time required to produce drug levels in the general circulation is a function of the device setup time, the time required for administration and the time required for the drugs to permeate through tissues. The pulmonary drug delivery via the DPET route is substantially faster in delivering drugs into the blood circulation than the IM route.

The DPET system greatly extends the maximum drug dosage that can be administered and absorbed by a human within seconds. By utilizing a propellant for drug dispersal, we can increase the dry powder drug payload dramatically. In preliminary studies, using the DPET system, we have successfully delivered 20 mg of epinephrine rapidly into the systemic circulation in normovolemic as well as in the compromised circulation CPR swine models. Increases in MAP were detected within 10-20 seconds post injection and peaked within 60 seconds post injection. The system would be useful to quickly administer large drug dosages which are required for nerve agent countermeasures. In addition, this system is not drug specific. The system could be used to deliver any number of drugs in dry powder form such as large dosages steroids or bronchodilators directly into the lung tissue to ameliorate the effects of toxic gas (e.g., chlorine or phosgene). This system has the potential to rapidly deliver nuclear, biological, and/or chemical (NBC) countermeasures to soldiers on the battlefield in a safe and non-invasive manner.

I. Nebulizer System

Turning now to the figures, FIGS. 1A-1C and 1D illustrate an exemplary dry powder administration system in accordance with the formulations and methods of the present disclosure. Such systems are capable of dispersing and propelling the dry powder formulations described herein for pulmonary insufflation.

FIGS. 1A-1C illustrates general experimental setup for the actuated, dry-powder administration of one or more therapeutic agents in dry-powder form by a pulmonary insufflation route. As shown in FIG. 1A, the exemplary dry powder administration system 10 comprises a syringe or replaceable/removable delivery tube 12 for delivery of the dry powder therapeutic formulation to the target, pulmonary region of a patient, a system body 20, preferably having an actuating means 14, such as a handle, and an connection system 16 allowing for attachment and removal of tube 12 from the system body 20. Suitable connection systems 16 include known connections, such as Swage-Lock systems and the like. As may be seen in the cross-sectional view of the system 10 of FIG. 1A illustrated in FIG. 1B, system body 20 comprises an interior valve system, having a valve means 22 such as a small ball valve, one or more liquefied gas reservoirs or chambers 24, and one or more dry powder drug reservoirs 26. The system 10 may be made from any number of appropriate materials, such as surgical steel, metals and metal alloys, plastics, polymers, and silicone-containing materials. The system 10 may also further comprise an endotracheal delivery tube 30, suitable for enhancing the delivery of the dry powder therapeutic agent into the endotracheal region or lung region of the subject.

As illustrated in the cross-sectional view of FIG. 1C, in typical use, the system shown therein comprises a body 20 with a valve means 22, such as a ball valve, that is charged with an appropriate liquefied propellant gas, such as R-134a. A dry powder therapeutic drug formulation, such as described in more detail below (e.g., epinephrine or an analog thereof), is micronized to the desired particle size (typically less than about 10 microns), and added into the reservoir portion of the system, adjacent to the liquefied gas reservoir. This is seen more clearly in the cross-sectional view of the system illustrated in FIG. 1B. Upon actuation of the valve means 22, the liquefied propellant gas and the dry powder therapeutic drug formulation are admixed, whereupon the gas simultaneously suspends and forces the dry powder out of the delivery device itself, through the delivery tube 12, and further into the lungs or endotracheal region of the subject patient, optionally using an ET tube 30 as shown, whereupon the therapeutic dry powder drug formulation is absorbed and begins to take therapeutic effect.

FIG. 1D illustrates a further, exemplary delivery system for the actuated, administration of dry-powder therapeutic formulations in accordance with the present disclosure. As illustrated in section "A" of the figure, the delivery system comprises at least two, separate chambers comprising at least one valve, one of which contains the dry, powdered drug or drug combination milled to an appropriate particle size, and the other of which comprises a liquefied propellant mixture, suitable for use in simultaneously dispersing and propelling the dry powder in the first chamber into the appropriate pulmonary region of the subject patient. Section "B" of FIG. 1D illustrates the interaction of the two separate chambers, whereupon when the valve is opened, fluid communication is established between the dry powder chamber and the propellant chamber, allowing the dry powder to admix with the liquefied propellant and become suspended in the liquefied gas. Finally, in section "C" of FIG. 1D, the final operation of the system is shown, following admixture of the propellant and drug formulation. As illustrated therein, when the propellant chamber valve is opened, the liquefied propellant/therapeutic drug admixture exits the device and forces the dry powder suspension out of the device and propels the aerosolized dry powder therapeutic agent through a delivery tube and into the endotracheal (ET) tube which has been inserted into the target region of the subject patient, and which acts to aid in the delivery of the dry powder therapeutic agent into the lungs or other pulmonary region of the subject, whereupon the dry powder therapeutic agent is absorbed.

In accordance with the systems and devices described herein, one or more propellants may be used to disperse and propel the dry powder therapeutic formulations into the pulmonary region of the subject patient. Suitable propellants include, but are not limited to, CFC propellants like trichlorofluoromethane and dichlorofluoromethane; non-CFC propellants like 1,1,1,2-tetrafluoroethane (R-134a, Norflurane), 1,1,1,2,3,3,3-heptafluoropropane (R-227), pentafluoro ethanol (R-125), 1,1,2-trifluoroethane (R-143), 1,1-difluoroethane (R-152a), and mixtures thereof; dimethyl ether; propane; butane; propane-butane mixtures; and combinations thereof. Preferably, and in accordance with one aspect of the present disclosure, the propellant is a non-CFC propellant, and more preferably, the propellant or propellant mixture comprises R-134a. The amount of the propellant component of the therapeutic systems described herein ranges from about 5 wt. % to about 90 wt %, depending upon the amount of dry powder therapeutic agent to be suspended and delivered to a patient.

II. Therapeutic Applications

The systems and methods described herein are useful in the pulmonary administration of therapeutic, dry-powder drug formulations into the endotracheal (ET) and lung regions of patients, for the purpose of treating a variety of lung and endotracheal injuries or disorders. Such injuries or disorders which are suitable for the application of the systems, methods, and therapeutic formulations described herein include, but are not limited to, toxic nerve agent poisoning; chemical poisoning or exposure; tuberculosis and diseases of the lungs caused by bacterium such as *Mycobacterium tuberculosis*; cystic fibrosis; cardiac arrest; asthma; and chronic obstructive pulmonary disease (COPD). As used herein, toxic nerve agent poisoning includes patient exposure to organophosphates, G-series nerve agents, V-series nerve agents, binary nerve agents, Soman [also known by its NATO designation, GD (o-pinacolyl methylphosphonofluoridate, or 3-(fluoromethyl-phosphoryl)oxy-2,2-dimethyl butane)], and chlorine gas, as well as combinations of such agents. Similarly, as used herein, chemical poisoning or exposure includes exposure to one or more compounds such as chlorine gas, bromine gas, phosgene, organophosphorus agents, and hypochlorites (OCls, i.e. NaOCl as a 5.25 wt. % solution, such as found in the commercial CLOROX™ product), such as encountered in commercial manufacturing operations, as well as in the home.

III. Formulation of Dry-Powder Drug Formulations

The therapeutic agent compositions which may be used in the nebulizer systems of the present disclosure are those compositions which are in micronized, dry powder form, and which may optionally comprise one or more additional formulation or drug-delivery systems or additives, in particular, drug delivery additives which are useful in association with the pulmonary system, including surfactants and mesoporous materials. Suitable classes of therapeutic agents which may be used, in micronized (e.g., having a particle size less than about 10 microns), dry powder from, include but are not limited to adrenergic agonists, steroids, antioxidants, antihistimines, anti-inflammatories (including NSAIDs), peptides, peptoids, and peptidomimetics, antibacterials and bacterial protein synthesis inhibitors, nerve agent therapeutic agents, interferons, bronchodilators, and anesthetics, alone or in combination (e.g., and without limitation, one or more adrenergic agonists and an anesthetic, or an andrenergic agonist, steroid, and anti-inflammatory). In accordance with one aspect of the present disclosure, the therapeutic agent is an adrenergic agonist.

Adrenergic agonists, such as β-2 agonists, suitable for use in the formulations and systems of the present disclosure include catecholamines and derivatives thereof, wherein the adrenergic agonists are selected from the group consisting of epinephrine, norepinephrine, α-methylnorepinephrine, isoproterenol, albuterol, aminophylline, beclomethasone, dyphylline, flunisolide, isoetharine, metaproterenol, oxtriphylline, terbutaline, theophylline, pseudoephedrine, phenylephrine, and ephedrine, alone or in combination, as well as the pharmaceutically-acceptable salts, solvates, hydrates, prodrugs, analogs, and polymorphs thereof. In accordance with one aspect of the present disclosure, the adrenergic agonists suitable for use as a therapeutic agent in the treatment of a patient in need of rescue therapy, such as undergoing an adverse bronchial or endotracheal event, is epinephrine or an analog thereof, norepinephrine or an analog thereof, or α-methylnorepinephrine or an analog thereof.

Antibacterials and bacterial protein synthesis inhibitors suitable for use in the dry powder formulations, systems, and methods of the present disclosure include but are not limited to nitroimidazoles; oxazolidinones; thiolactins; nitroimidazopyrans; rifamycins, including rifampin (RIF), rifabutin, and rifapentine; pyrazinamide (PZA); ethambutol (EMB); isoniazid (INH); and fluoroquinolines, such as ciprofloxacin, ofloxacin, sparfloxacin, levofloxacin, moxifloxacin, and gatifloxacin, alone or in combination, as well as the pharmaceutically-acceptable salts, solvates, hydrates, prodrugs, and polymorphs thereof.

Toxic gas/nerve gas therapeutic agents suitable for use in the dry powder formulations, systems, and methods of the present disclosure include but are not limited to those agents known to exhibit a therapeutic effect on patients suffering from toxic gas/nerve gas/nerve agent exposure, including albuterol; $\beta_2$-agonists, in particular epinephrine, norepinephrine, α-methylnorepinephrine, and analogs thereof; ipratropium; steroids; thienylcyclohexylamines; anticholinesterases such as pyridostigmine bromide (PB, 3-hydroxy-1-methylpyridinium bromide dimethylcarbonate); pralidoxime (2-PAM); diazepam; lorazepam; midazolam; hexamethylenetetramine (HMT); urotropin; methenamine; and combinations thereof, as well as the pharmaceutically-acceptable salts, solvates, hydrates, prodrugs, and polymorphs thereof.

Other therapeutic agents which may be included in the dry powder therapeutic formulations of the present disclosure are anesthetics, such as lidocaine, veratridine, and the like, without limitation.

Any suitable pharmaceutically effective drug which is used for the treatment of a respiratory disease may also be co-administered with the therapeutic compositions of the present disclosure. For example, $\beta_2$-agonists, e.g. epinephrine, norepinephrine, α-methylnorepinephrine, or analogs thereof, may be formulated for co-administration with an anticholinesterases composition. Additional anti-muscarinic compounds may also be co-administered. For example, ipratropium (e.g. ipratropium bromide) or tiotropium may be administered. Isomers, salt forms or counterion formulations of the antimuscarinic compounds are all within the scope of the present disclosure. These may be in their natural form, or in a controlled release formulation, although the natural form is preferred.

Additional therapeutics including steroids may also be co-administered with the dry powder therapeutic formulations of the present disclosure, or equivalently may be milled to the appropriate particle size as disclosed herein and admixed with the primary therapeutic agent to form the therapeutic formulation and compositions useful in treating pulmonary-based injuries or disorders. Examples of suitable steroids for use with the therapeutic compositions described herein include but are not limited to androstanes, beclomethasone, dipropionate and fluticasone. Other suitable therapeutics which may be co-administered include but are not limited to mucolytics, matrix metalloproteinase inhibitors, leukotrienes, antibiotics, antineoplastics, peptides, vaccines, antitussives, nicotine, phosphodiesterase 4 (PDE4) inhibitors as well as inhibitors of any of the four sub-types (A-D) of PDE4, elastase inhibitors, and sodium cromoglycate.

The dry powder therapeutic formulations of the present disclosure are preferably administered, using the systems described above (e.g., $\beta_2$ agonists alone or in combination), in large doses, such large doses preferably ranging from about 1 mg to about 1,000 mg per dose, more preferably from about 20 mg to about 1,000 mg per dose, as well as in dose ranges in between these values, such as from about 100 mg to about 1,000 mg, and about 600 mg to about 900 mg, in example and without limitation. Exemplary dosages include but are not limited to about 25 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 975 mg, about 990 mg, and about 1,000 mg per dose, as well as amounts greater than 1,000 mg per dose (in such circumstances as may require it), and in dosage amounts in ranges between any two of these values, e.g., from about 40 mg per dose to about 250 mg per dose, without limitation. Such dosages of dry powder therapeutic agents are also preferably micronized, or milled, to an average particle size less than about 10 microns (10 μm), such preferred average particle sizes ranging from about 0.1 μm to about 10 μm, as well as values in between, such as from about 0.5 μm to about 10 μm, and from about 0.2 μm to about 5 μm, and from about 1 μm to about 5 μm. In one preferred aspect of the present disclosure, the dry powder therapeutic agents and/or formulation composition is micronized to an average particle size less than about 5 microns (5 μm), and more preferably less than about 3 microns (3 μm) in particle size. In accordance with further aspects of the present disclosure, the particles of dry powder therapeutic agents suitable for use in the delivery systems described herein may have, in addition to the particle size ranges outlined herein, densities below about 1 $g/cm^3$, and more preferably below about 0.5 $g/cm^3$, and/or mean mass aerodynamic diameter (MMAD) values between about 0.1 μm and about 10 μm, more preferably from about 1 μm to about 5 μm, in order to achieve higher respirable fraction and avoid the natural clearance mechanisms of the lungs often attributed to/associated with higher geometric diameter (>10 μm) of the particles. In general, the dry powder therapeutic agents, and the formulations described herein comprising such agents, may have a broad particle size distribution (PSD) ranging from a few nanometers to several micrometers, as will depend upon the specific formulation and therapeutic application.

The compositions of the present disclosure comprise therapeutic agents or biologically active substances in dry powder form, which may be water-soluble, water insoluble, oil-soluble, oil-insoluble, organic solvent soluble or insoluble drugs, or lipid-soluble drugs and biologically active substances, optionally in combination with one or more formulating agents, such as appropriate surfactants which are useful in the introduction of the therapeutic agent into the bronchial or endotracheal (pulmonary) region of the patient. In accordance with one aspect of the present disclosure, the therapeutic compositions can comprise one or more therapeutic agents alone or in combination with an appropriate propellant. In accordance with one aspect of the present disclosure, the compositions can comprise a water-insoluble or substantially water-insoluble drug or biologically active substance and one or more fatty acids. In a further aspect, the compositions can comprise a water-insoluble or substantially water-insoluble drug or biologically active substance, one or more fatty acids, and one or more surfactants. In yet another aspect, the compositions suitable for use with the nebulizer assemblies of the present disclosure can comprise a water-insoluble or substantially water-insoluble drug or biologically active substance, water, and at least one gelling agent.

The therapeutic compositions disclosed herein, according to the present invention, may be comprised of one or more drugs alone or as part of a mixture of a biologically active substance, optionally with a carrier or adjuvant, emulsifier, one or more different drugs, polymers, excipients, coatings and combinations thereof. In essence, the drug(s) or substances can be combined with any combination of pharmaceutically acceptable components so as to be effectively delivered in dry powder form to the cellular surfaces within the pulmonary system of a patient by the method described herein, e.g., pulmonary drug delivery. The drug(s) is typically not dissolved in a drug delivery medium solvent, as dry powder therapeutic agent formulations are preferred, but can be suspended or emulsified in a solvent or medium during the processing as appropriate. Such formulation mediums can take the form of an aqueous mixture, oil, or an organic liquid, so long as the final therapeutic agent composition delivered to the patient is in dry powder form. The delivery media solution can also comprise microspheres or nanospheres of biologically active substances, as appropriate.

In accordance with certain aspects of the present disclosure, the dry powder therapeutic agent formulations disclosed herein may further comprise one or more drug delivery systems or agents, to enhance or control the rate and period of drug delivery into the pulmonary system of the subject's body. In accordance with one specific aspect, the dry powder formulations may comprise mesoporous materials, including those derived from supra-silica mesoporous matrices, and having one or more of the following features—an ordered pore network, which is substantially homogenous in size and allows for fine control of the drug load and release kinetics; a high pore volume, so as to allow for the hosting of the required amount of the therapeutic agents; a high surface area, which may translate into high potential for drug absorption; and/or a silanol-containing surface, especially one which is capable of being functionalized to allow for better control over the drug loading and release, as well as combinations of such features. Exemplary mesoporous materials suitable for use in the dry powder therapeutic compositions of the present disclosure include, but are not limited to, MCM-41, MCM-41-$NH_2$, MCM-$41_{12}$, MCM-$41_{16}$, MCM-48, MSU-3, SBA-15, SBA-15-$NH_2$, SBA15/PLGA, SBA-15-C8, SBA-15-C18, SBA-15 with PDDA, FSM, MIL-100, MIL-101, LP-la3d, LP-la3d-C8, and combinations thereof.

The compounds, particularly the therapeutic agents themselves, useful in the formulations and therapeutically-useful compositions of the present invention can be used in the natural form, as discussed herein, or in the form of pharmaceutically acceptable salts derived from inorganic or organic acids. The term "pharmaceutically acceptable salt" as used herein is meant to refer to those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (WileyVCH, Zunch, Switzerland: 2002). The salts can be prepared in situ during the final isolation and purification of the compounds of the present invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, flimarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final preparation, formulation, or purification of the therapeutically-useful compounds, substantially water-insoluble compounds described for use in aspects of this disclosure by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Pharmaceutically acceptable salts of compounds which may be used in formulations and systems described herein may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids can also be made.

The formulations described for use herein may conveniently be presented in unit dosage form and may be prepared by any of the methods well known in the art of pharmacy. All methods for formulation in association with the presently disclosed therapeutic agents may include a step of bringing into association one or more of the compounds described herein, or a pharmaceutically acceptable salt or solvate thereof (the "active ingredient"), with a carrier which constitutes one or more accessory ingredients. In general, the formulations may be prepared by uniformly and intimately bringing into association the active ingredient with liquid carriers or finely divided solid carriers or both and then, if necessary, shaping the product into the desired formulation.

The compound or a pharmaceutically acceptable ester, salt, solvate or prodrug thereof, such as a pharmaceutically acceptable ester, salt, solvate, or prodrug of epinephrine or its analogs, norepinephrine or its analogs, budesonide, glutathione, or other $\beta_2$-adrenoceptors/$\beta_2$AR agonists can be admixed with other active materials that do not impair the desired action, or with materials that supplement the desired action, including other drugs against inflammatory disease or lung injury.

The therapeutic agents suitable for use as pulmonary-acting, dry powder delivery drugs in the medicament compositions of the present disclosure may also optionally include one or more added, secondary therapeutic agents, alone or in combination, including but are not limited to, vitamins, antioxidants, anti-bronchitus agents, anti-pneumonia agents, pulmonary anti-cancer agents, antianginal agents, antihypertensive agents, and combinations thereof. In accordance with one aspect of the present disclosure, the preferred drug is a vitamin or a combination of two or more vitamins. Suitable vitamins for use herein include but are not limited to Vitamin A, Vitamin B (including Vitamin $B_{12}$), Vitamin C, Vitamin D, Vitamin E, Vitamin K3 (menadione; 1,4-dehydro-1,4-dioxo-2-methyl-naphthalene, MNQ), retinol, riboflavin, niacin, ascorbic acid, β-carotene, and Coenzyme Q, including various derivatives of Coenzyme Q having various isoprenoid side chains, including but not limited to QH, $QH_2$, $Q_3$ and $Q_{10}$.

In accordance with further aspects and embodiments of the present disclosure, the compositions may comprise antianginal and/or antihypertensive drugs or biologically active agents which are insoluble or substantially insoluble in water, or exhibit poor water solubility (e.g., less than about 5 mg/mL), and therefore are good candidates for preparing dry powder therapeutic formulations such as disclosed herein. Compounds of these types suitable for use herein include inhibitors of cAMP (3',5'-cyclic adenosine monophosphate), cGMP (3',5'-cyclic guanosine monophosphate), inhibitors of cGMP-specific phosphodiesterase type IV (PDE IV), inhibitors of c-GMP-specific phosphodiesterase type V (PDE V), drugs that may exhibit anti-anginal effects, including drugs which exhibit therapeutic effects on angina pectoris, and compounds which can enhance the natriuretic effect of atrial natriuretic peptide (ANP). Suitable examples of such drugs include but are not limited to atenolol, amlodipine, diltiazem, eplerenone, naphthyriclin-4-one derivatives, griseolic acid, dihydrodesoxygriseolic acid, derivatives of griseolic acid and dihydrodesoxygriseolic acid, angiotensin converting enzyme inhibitors, todalafil, vardenafil, ranolazine [see, Tafreshi, M. J., et al., *Ann. Pharmacother*., Vol. 40(4): pp. 689-693 (2006)], sildenafil, sildenafil citrate (Viagra®; Pfizer, Inc., New York), N-desmethyl sildenafil, and T-1032 (methyl-2-(4-aminophenyl)-1,2-dihydro-1-oxo-7-(2-pyridinyl-methoxy)-4-(3,4,5-trimethoxyphenyl)-3-isoquionoline carboxylate sulfate; see: Noto, T., et al., *J. Pharm. Exp. Ther*., Vol. 294(3): pp. 870-875 (2000)], as well as derivatives, solvates, prodrugs, and polymorphs thereof. In accordance with one aspect of this embodiment, the drug is a catecholamine, such as metaproterenol, albuterol, phenylephrine, or an analog thereof. Such drugs may be used in a therapeutically effective amount ranging from about 1 mg/kg/d to about 1,000 mg/kg/d, or alternatively in therapeutic amounts ranging from about 20 mg/dose to about 1,000 mg/dose, as well as therapeutically effective amounts within this range, e.g., about 25 mg/dose, about 30 mg/dose, about 50 mg/dose, about 100 mg/dose, and about 250 mg/dose, without limitation.

Naturally-occurring fats and oils may optionally be used, as appropriate, in order to aid in the formulation of the dry powder therapeutic agent compositions of the present disclosure. "Naturally-occurring fats and oils" as used herein refers to the glyceryl esters of fatty acids (i.e., triglycerides) normally found in animal or plant tissues, including those which have been hydrogenated to reduce or eliminate unsaturation. Naturally occurring fats and oils include vegetable oils such as linseed oil, soybean oil, sunflower seed oil, corn oil, sesame oil, olive oil, castor oil, coconut oil, palm oil, peanut oil, jojoba oil, neem oil, and macadamia nut oil. The amount of such fats and/or oils which may be used in the formulation will vary depending upon the individual characteristics of the oil or fat, but is typically an amount such that the final, powder-form therapeutic composition is "dry" in that it has a moisture content preferably less than about 10 wt. % water.

In accordance with further aspects of the present disclosure, the formulations of the present disclosure may also optionally comprise hylauronic acid in an amount suitable to minimize water from transpiring across the droplets formed by the nebulizer.

The dry powder therapeutic compositions of the present invention may further optionally comprise one or more preservatives. As used herein, the term "preservative" is intended to mean a compound used to prevent the growth of microorganisms. Such preservatives which may be used in the dry powder therapeutic compositions described herein for use in pulmonary disorders or patients suffering a pulmonary inflammatory response to an external chemical agent (e.g., chlorine gas), when included, are included as additives at typical concentrations in accordance with current pharmaceutical practices [see: *The United States Pharmacopeia-National Formulary,* 29th Edition, (2006) Rockville, Md.; and, *Remington's Pharmaceutical Sciences,* 21st Edition, Troy, D B, Ed. Lippincott, Williams and Wilkins; (2005)]. Exemplary preservatives which may be used with the dry powder compositions and systems of the present disclosure include but are not limited to antifungal and antimicrobial preservatives, such as benzoic acid, hydroxy benzoate and its derivatives, butylparaben, ethylparaben, methylparaben, propylparaben, sodium benzoate, benzalkonium chloride, benzethonium chloride, benzyl alcohol, cetylpyridinium chloride, chlorobutanol, phenol, phenylethyl alcohol, phenylmercuric nitrate and thimerosal; and antioxidants, such as ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, and sodium metabisulfite, as well as combinations of two or more of the these preservatives.

The dry powder therapeutic compositions and formulations of the present invention may also further comprise one or more pH modifying agents (buffering agents), in order to maintain the pH of the composition in the desired range, e.g., from a pH of from about 3.5 to about 8. pH modifying agents suitable for use herein, include, but are not limited to, inorganic salts, alkali earth and/or alkali rare earth hydroxides (e.g., NaOH, KOH, or CsOH); carbonate or bicarbonate of any appropriate alkali or alkali rare earth metal (e.g., $Na_2CO_3$, $K_2CO_3$, $NaHCO_3$, and $KHCO_3$); phosphates, such as calcium hydrogen phosphate, potassium metaphosphate, and potassium phosphate monobasic; inorganic acids such as hydrochloric acid (HCl), and organic acids such as acetic acid, citric acid, succinic acid, fumaric acid, malic acid, maleic acid, glutaric acid or lactic acid, as well as combinations thereof, any of which may be water-soluble or water-insoluble, anhydrous or hydrated (e.g., dehydrate, sesqui-hydrate, or semi-hydrate), as appropriate.

Others components which may be included in the therapeutically useful compositions of the present disclosure include but are not limited to binding materials (e.g., block polymers, natural and synthetic rubber, polyacrylates, polyurethanes, silicones and styrene-butadiene copolymers); colorants, including but not limited to FD & C yellow #6, FD & C red #40, FD & C blue #2, and FD & C violet #1, as well as any other appropriate dye or combination of dyes; and, UV inhibitors, to inhibit UV decomposition or isomerization of the therapeutic compositions.

Other pharmaceutically acceptable formulation excipients may also be used in accordance with the formulation compositions described and disclosed herein, including but not limited to coatings, stabilizers, emulsifiers, and the like, such as those described in "*The Handbook of Pharmaceutical Manufacturing Formulations*" [Niazi, S. K., CRC Press (2004)], so long as the final product prior to administration to a patient is in dry powder form. Additionally, and in accordance with aspects of the present disclosure, one or more surface active agents (surfactants) may be added to the formulation compositions as appropriate. Although not required, incorporation of a compatible surfactant can improve the stability of the instant respiratory dispersions, increase pulmonary deposition and facilitate the preparation of the suspension. Moreover, by altering the components, the density of the particle or structural matrix may be adjusted to approximate the density of the surrounding medium and further stabilize the dispersion. Any suitable surface active agent (surfactant) may be used in the context of the present invention, provided that the surfactant is preferably physiologically acceptable. Physiologically acceptable surfactants are generally known in the art and include various detergents and phospholipids, as discussed in more detail below. In accordance with one aspect, it is preferred that the surfactant is a phospholipid including, but not limited to, an extract of a natural surfactant such as any number of known pulmonary surfactants, including bovine- and calf-lung surfactant extracts, an egg phospholipid, a vegetable oil phospholipid such as a soybean phospholipid, or phosphatidylcholine. Preferably, in accordance with aspects of the present disclosure, the surfactant suitable for use with the therapeutic compositions of the present disclosure is an extract of a natural surfactant, an egg phospholipid, or combinations thereof. More preferably, the compositions may any one or more of a number of biocompatible materials as surfactants, such as surfactants comprising phospho lipids.

In a broad sense, surfactants suitable for use in the present invention include any compound or composition that aids in the formation and maintenance of the stabilized respiratory/pulmonary dispersions by forming a layer at the interface between the particles of therapeutic compound (e.g., epinephrine, terbutaline, atropine, or pralidoxime chloride) and the suspension medium. The surfactant may comprise a single compound or any combination of compounds, such as in the case of co-surfactants. In accordance with certain aspects of the present disclosure, depending upon the specific therapeutic composition or formulation, preferred surfactants include but are not limited to those surfactants that are substantially insoluble in the medium, nonfluorinated, and selected from the group consisting of saturated and unsaturated lipids, especially those that are obtained or extracted from natural sources, nonionic detergents, nonionic block copolymers, ionic surfactants, and combinations of such agents. It should be emphasized that, in addition to the aforementioned surfactants, suitable (i.e. biocompatible) fluorinated surfactants are compatible with the teachings herein and may be used to provide the desired stabilized therapeutic preparations.

Lipids, including phospholipids, from both natural and synthetic sources are particularly compatible with the present inventions and may optionally be used herein in varying concentrations so as to aid in forming the particle or structural matrix that is most useful (with regard to delivery and administration) in the final, therapeutic compositions. Generally compatible lipids include those that have a gel to liquid crystal phase transition greater than about 40° C. Preferably, and as described in more detail below, the incorporated lipids are relatively long chain (i.e. $C_{16}$-$C_{22}$) saturated lipids and preferably comprise one or more phospholipids. Exemplary phospholipids useful in the disclosed stabilized preparations of the present invention comprise egg phosphatidylcholine, dilauroylphosphatidylcholine, dioleylphosphatidylcholine, dipalmitoylphosphatidylcholine, disteroylphosphatidylcholine, short-chain phosphatidylcholines, phosphatidylethanolamine, dioleylphosphatidylethanolamine, phosphatidylserine, phosphatidylglycerol, phosphatidylinositol, glycolipids, ganglioside GM1, sphingomyelin, phosphatidic acid, cardiolipin; lipids bearing polymer chains such as polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate. Due to their excellent biocompatibility characteristics, phospholipids and combinations of phospholipids and poloxamers are particularly suitable for use in the stabilized dispersions disclosed herein. With regard to biologically-compatible surfactants comprising phospholipids, in accordance with certain aspects of the present disclosure, it is preferable that such biologically-compatible surfactants for use with the therapeutic compositions described herein, especially those comprising tocopherol and/or gamma-tocopherol, include those surfactants that are extracts of natural surfactants, in particular pulmonary surfactants, and synthetic synthesized mixtures of pulmonary surfactants in order to mimic natural lung surfactant. Exemplary surfactants suitable for use with the present compositions of dry powder therapeutic formulations, such as $\beta_2$-agonists and the like, include but are not limited to SURVANTA® (beractant, available from the Ross Products Division of Abbott Laboratories), a bovine-lung pulmonary surfactant comprising phospholipids, neutral lipids, fatty acids, and surfactant-associated proteins; SURFAXIN® (lucinactant, available from Discovery Laboratories, Inc.); INFASURF® (calfactant, available from Forest Pharmaceuticals, Inc., St. Louis, Mo.), an extract of natural surfactant from calf lung which includes phospholipids, neutral lipids, and hydrophobic surfactant-associated proteins B and C(SP-B and SP-C); CUROSURF® (poractant alpha, available from Chiesi Farmaceutici, S.p.A., Parma, Italy), a non-pyrogenic pulmonary surfactant that is an extract of natural porcine lung comprising polar lipids (mainly phospholipids) and hydrophobic low molecular weight proteins (surfactant associated proteins SP-B and SP-C); and ALVEOFACT® (available from Boehringer Ingelheim Pharma, Ingelheim, Germany), a natural bovine extract/surfactant comprising bovine lung phospholipids; as well as the synthetic pulmonary surfactants EXOSURF®, VENTICUTE®, ADSURF® (Pumactant™), and KL-4, all of which synthetic surfactants comprise the phospholipid dipalmitoylphosphatidylcholine (DPPC).

Compatible nonionic detergents for use in the dry-powder formulations of the present disclosure comprise, without limitation, sorbitan esters including sorbitan trioleate (SPAN™ 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents include any of those which can be easily identified using "McCutcheon's Emulsifiers and Detergents" (McPublishing Co., Glen Rock, N.J.) which is incorporated herein in its entirety. Preferred block copolymers include but are not limited to diblock and triblock copolymers of polyoxyethylene and polyoxypropylene, including poloxamer 188 (PLURONIC™ F-68), poloxamer 407 (PLURONIC™ F-127), and poloxamer 338. Ionic surfactants such as sodium sulfosuccinate, and fatty acid soaps may also be utilized. In accordance with certain aspects and embodiments of the present disclosure, the therapeutic compositions described herein may comprise oleic acid or its alkali salt.

Those skilled in the art will further appreciate that a wide range of surfactants, including those not listed above, may optionally be used in conjunction with the formulations and systems of the present invention. Moreover, the optimum surfactant, or combination thereof, for a given application can readily be determined by empirical studies that do not require undue experimentation. It will further be appreciated that, the preferred insolubility of any incorporated surfactant in the suspension medium will dramatically decrease the associated surface activity. As such, it is arguable as to whether these materials have surfactant-like character prior to contracting an aqueous bioactive surface (e.g. the aqueous hypophase in the lung).

On a weight to weight basis, the instant formulations and compositions of the therapeutic compositions comprising dry powder therapeutic agents suitable for use in pulmonary therapy applications may comprise varying levels of surfactant. In this regard, the compositions and formulations described herein which include one or more surfactants will preferably comprise greater than about 0.1%, about 1%, about 5%, about 10%, about 15%, about 18%, or even about 20% w/w % surfactant. In accordance with a further aspect of the present disclosure, the therapeutic compositions and formulations described herein may comprise greater than about 25%, about 30%, about 35%, about 40%, about 45%, or about 50% w/w surfactant. Still other exemplary embodiments of the present disclosure will include therapeutic compositions and formulations as described herein, further comprising one or more surfactants, wherein the surfactant or surfactants are present at greater than about 55%, about 60%, about 65%, about 70%, about 75%, about 80%, about 85%, about 90% or even about 95% w/w.

In certain embodiments of the present disclosure, a novel therapeutic composition comprising one or more lipids associated with at least one appropriate therapeutic agent is contemplated. A lipid as referred to herein is a substance that is characteristically insoluble in water and extractable with an organic solvent. Lipids include, for example, the substances comprising the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. Of course, compounds other than those specifically described herein that are understood by one of skill in the art as lipids are also encompassed by the compositions and methods of the present invention.

A lipid for use with the present disclosure may be naturally occurring or synthetic (i.e., designed or produced by man). However, a lipid is typically a biological substance. Biological lipids are well known in the art, and include for example and without limitation, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof.

The following examples are included to demonstrate preferred embodiments of the invention. It should be appreciated by those of skill in the art that the techniques disclosed in the examples which follow represent techniques discovered by the inventor(s) to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Epinephrine Investigative Study

Figure 2:
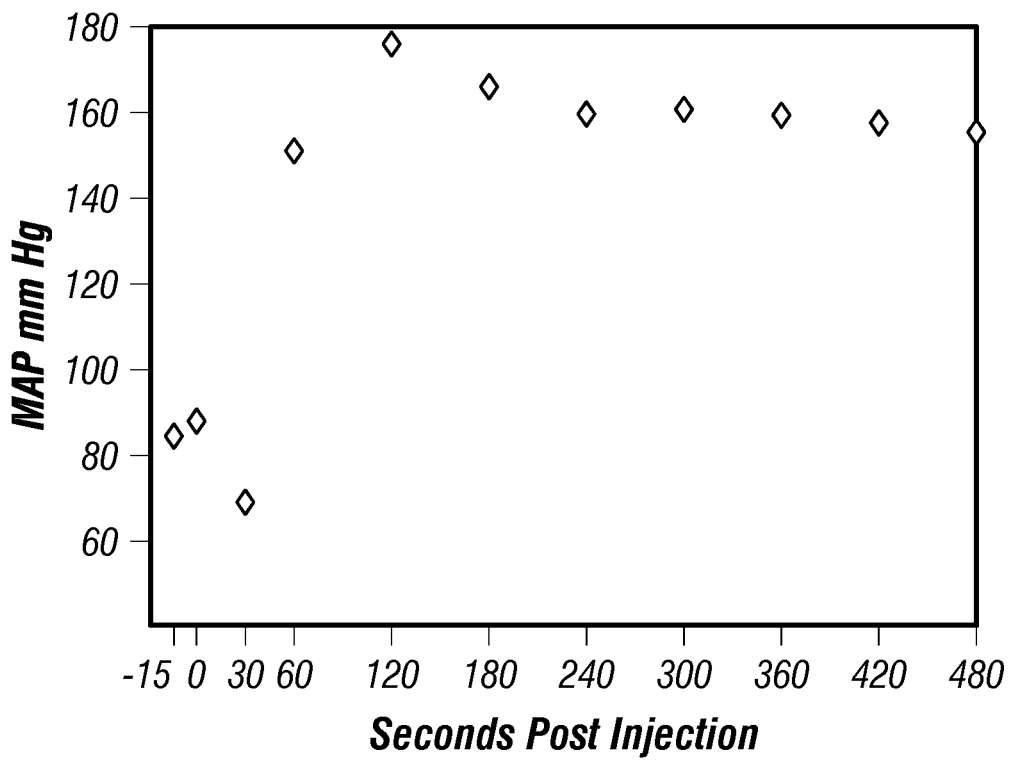
FIG. 2 illustrates a plot of MAP versus injection time, illustrating epinephrine delivery in normovolemic anesthetized swine.
Figure 3:
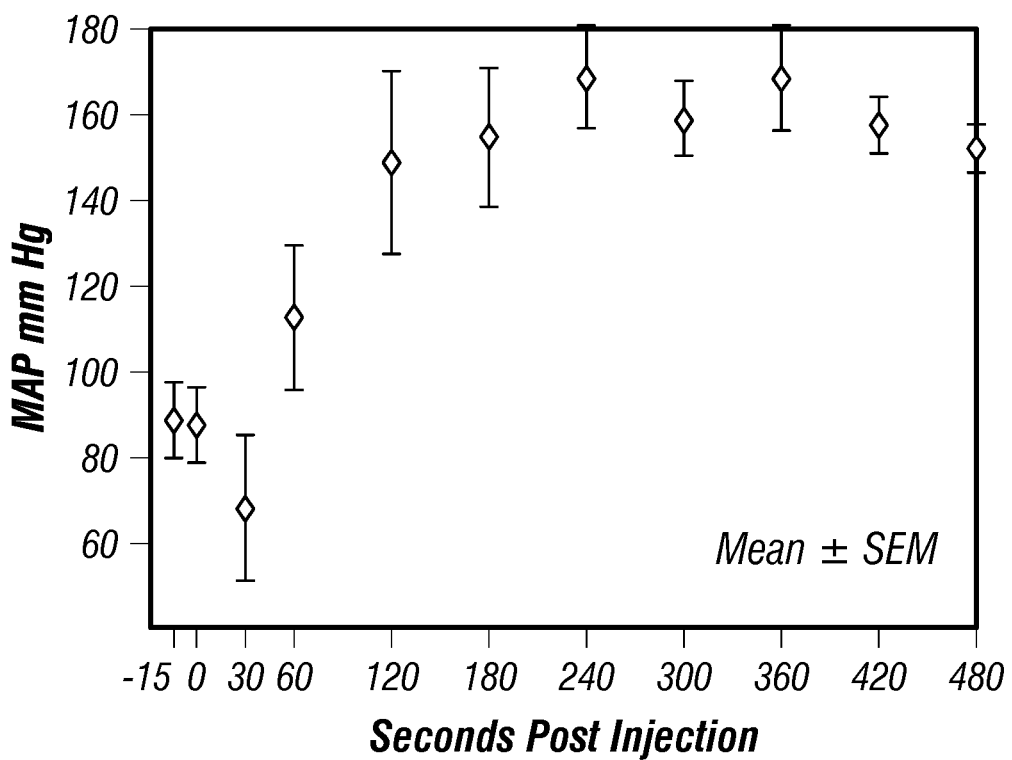
FIG. 3 illustrates a plot of MAP vents injection time, illustrating the increase in average MAP post-DPET (dry powder endotracheal) injection.
Figure 4:
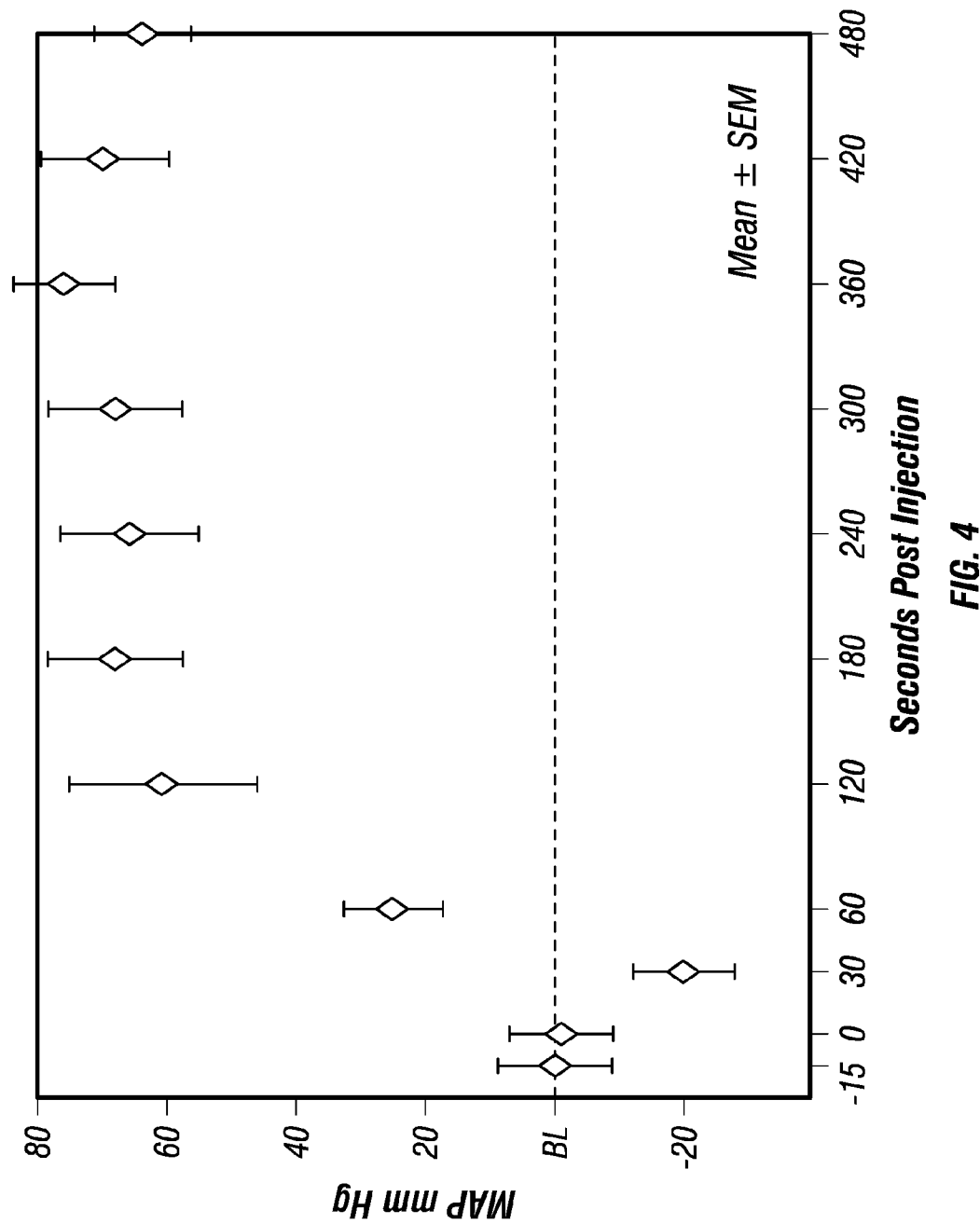
FIG. 4 illustrates the effect of epinephrine delivered by the DPET route of the present disclosure on MAP relative to baseline.

The rapid uptake of epinephrine via a DPET (dry powder endotracheal drug delivery) method in a normovolemic swine model (n=5) was demonstrated, using experimental methods according to established procedures, such as those described by Wang, et al. [*Intensive Care Med.*, Vol. 28, pp. 352-357 (2002)], and Zanen, et al. [*Int. J. Pharm.*, Vol. 114, pp. 111-115 (1995)]. FIG. 2 illustrates a representative experiment showing the increase in MAP in normovolemic anesthetized swine. As can be seen from the figure, this plot demonstrates that a relatively large dose of dry powder epinephrine (e.g., ≥20 mg) can be insufflated into the lung and be absorbed and placed into the circulating blood within 10 to 20 seconds of administration. The standard IV dosage was used for both CV and DPET routes. At 30 s post-injection an increase in MAP was detected, as illustrated in FIG. 3. Epinephrine delivered by the DPET route described herein increased MAP by more than 60 mmHg over baseline from 60-480 s post injection, as is shown in FIG. 4. Sustained MAP above 60 mmHg was generated by epinephrine delivery by the DPET route at a drug concentration only half of that used in standard ET epinephrine administration (0.4 mg/kg in swine). The micronization (e.g., 1-5 μm) of the drug and use of a propellant for delivery makes delivery by this method far more effective than delivery by the standard ET route, which utilizes a liquid bolus delivered by syringe.

Figure 5:
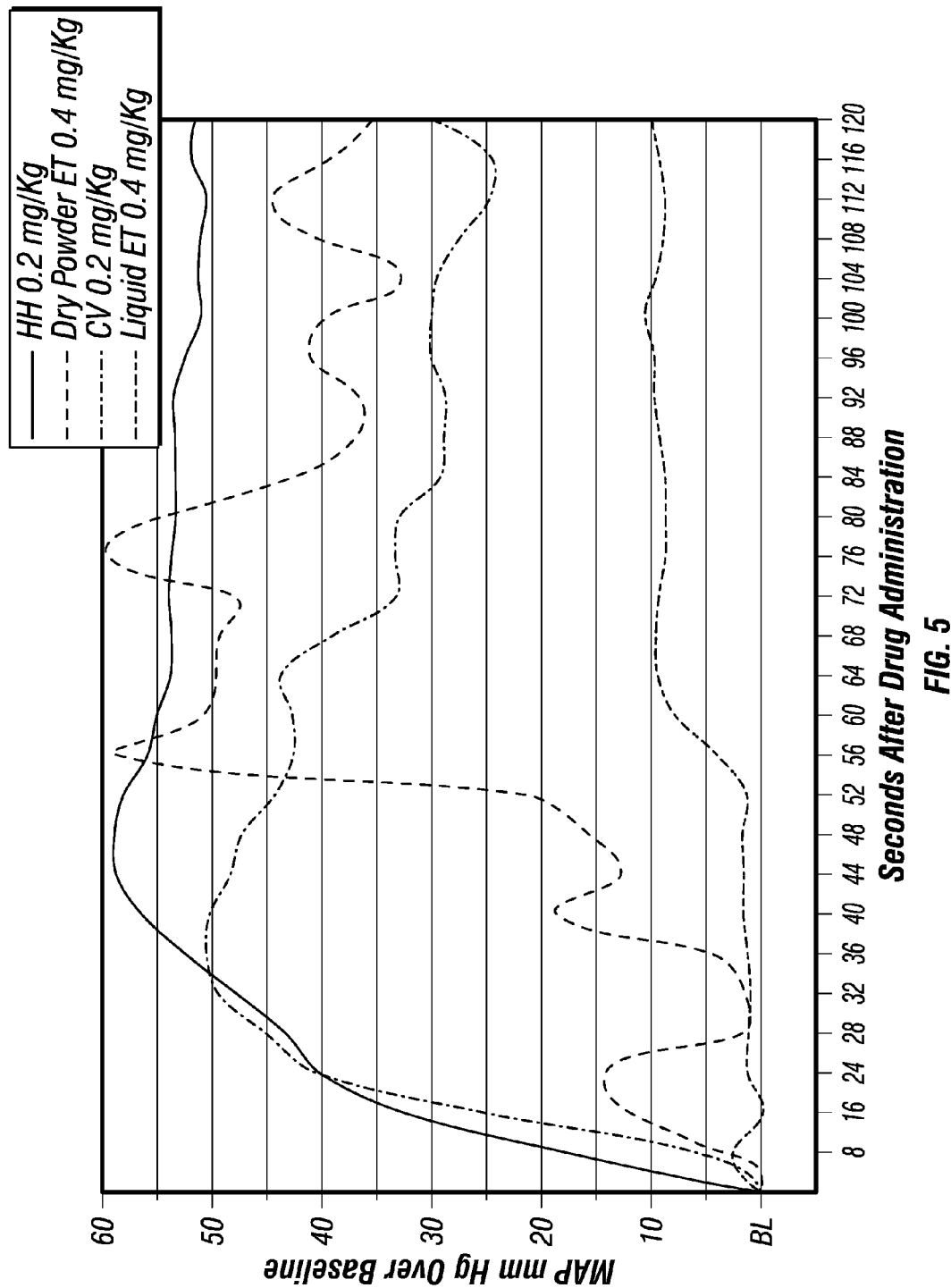
FIG. 5 illustrates the effect of epinephrine on MAP over baseline for the CV, IO, ET, and DPET routes.
Figure 6:
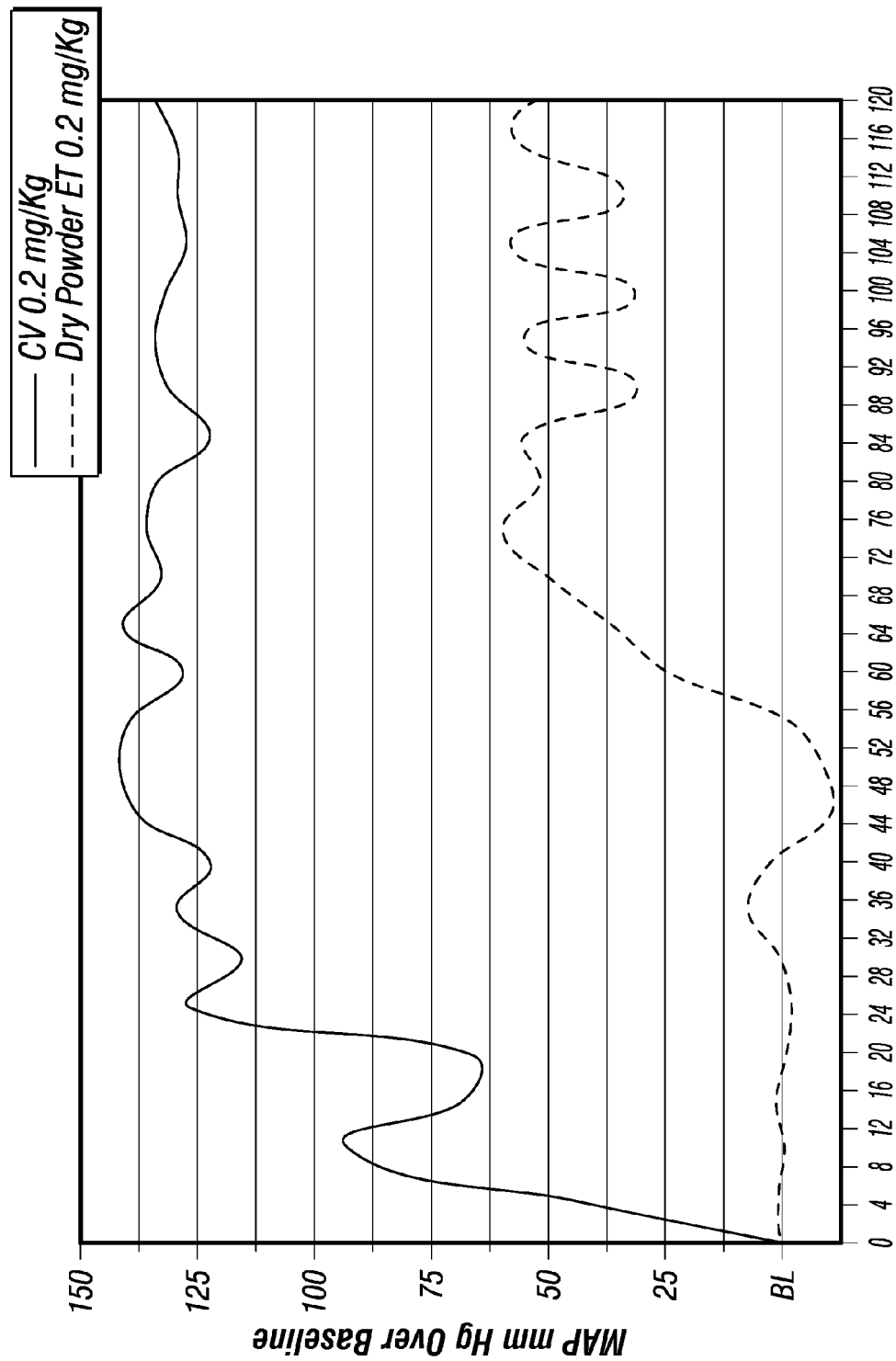
FIG. 6 illustrates the demonstrated a rapid uptake of epinephrine via a DPET method in a normal beating heart swine model.

FIG. 5 and FIG. 6 illustrate MAP following epinephrine in a cardiac arrest swine model, and in a normal pig model. FIG. 5 shows an increase in MAP following epinephrine delivery in a swine model of a cardiac arrest event using various drug-delivery routes. Increases in MAP above the CPR baseline (38-52 mm Hg) were detected over an 8 minute time course post-injection. CV is represented by the red line, IO by the black line in the figure, DPET MAP values over time by the blue line in the figure, and the standard ET is represented by the green line. HH refers to the humeral head, central venous. FIG. 6 illustrates increased MAP following epinephrine delivery in normal and anesthetized swine. Increased MAP is detected over an 8 minute time course, post-injection. Drug delivery is by CV (red line) or DPET (blue line, "Dry Powder ET"), and the MAP is displayed as above baseline (122-128 mm Hg).

This study using a dry powder endotracheal drug delivery system (DPET) of the present disclosure in a swine model of cardiac arrest illustrates several advantages of the currently disclosed compositions, systems, and methods. Physiological effects (measured as increase in Mean Arterial Pressure (MAP) over baseline MAP) from DPET injection of epinephrine were detected in <20 seconds. MAP peaked at 90 mmHg at a sustained pressure of greater than 50 mmHg over baseline within 80 seconds.

Example 2

Exemplary (Prophetic) General Procedure

We have substantial experience with acute swine studies and our experimental protocols are similar to other leading CPR researchers, such as described in the Wang and Zolen articles, referenced supra. Pigs will be sedated and intravenous (IV) access via a peripheral ear vein will be used to infuse alpha-choralose for general anesthesia. Pigs will be orotracheally intubated and ventilated with room air, using a volume-cycled ventilator (Harvard Apparatus, South Natick, Mass.). Ventilation will be begun at a tidal volume of 15-20 cc/kg, a rate of 12-16 breaths/min. Ventilation will be adjusted to maintain end-tidal carbon dioxide between 35 to 45 torr as measured with a Datex capnometer, such as the MULTICAP® or NORMOCAP® capnometers (available from Datex Instrumentarium Corp., Helsinki, Finland). Core body temperature will be measured from the pulmonary arterial catheter and will be maintained by use of a heating blanket as needed. We will secure three surface electrodes configured to correspond to a standard Lead II electrocardiogram (ECG). We will monitor and record this continuously using HP monitor and then will digitize the signal at 1000 Hertz and record it along with hemodynamic variables on Sony VIAO PC using Chart Pro 5.5/Cardiovascular module software or the equivalent.

After the airway is secured and surgical depth anesthesia is established the femoral artery will be cannulated with a PiCCO® (Pulson Medical Systems AG, Munich, Switzerland) catheter which will allow us to monitor and arterial pressure and continuous cardiac output. A cut-down on the right side of the neck of the pigs will be performed in order to cannulate the external carotid artery for aortic blood sampling to measure arterial blood gases and lactate using an i-STAT® analyzer (Abbott Point of Care, East Windsor, N.J.) and for placement of a sheath introducer (7.5 F) in the internal jugular vein. A pulmonary arterial catheter (Swan-Ganz, available from Baxter Medical) will be placed through the introducer sheath for monitoring and recording right atria pressure, pulmonary artery pressure, temperature and sampling mixed venous blood. A Millar catheter (Millar Instruments, Inc., Houston, Tex.) will be advanced from the left carotid to the left ventricle to continuously monitor and record left ventricular end diastolic pressure (LVEDP). Coronary perfusion pressure will be calculated from diastolic aortic pressure minus LVEDP. Positioning of the catheters will be confirmed by the pressure tracing, and at post-mortem. All pressures will be recorded at 1000 Hertz using Chart Pro software (Critical Tools, Inc., Austin, Tex.) and a PowerLab analog-to-digital converter (ADInstruments).

After a 30 min period of stable hemodynamics, baseline hemodynamics will be recorded and blood samples will be obtained. Animals will then receive 10,000 units of heparin to facilitate blood sampling during CPR. Induction of ventricular fibrillation (VF) will be achieved with a central venous administration of 10 mL of saturated potassium chloride. VF will be confirmed by examination of the ECG tracing and the absence of pulses in the arterial pressure waveform.

Aerosol delivery of epinephrine requires that the dose be concentrated into a small volume, e.g., <2 ml, for effective delivery. Epinephrine bitartrate salt (Sigma) is highly soluble in water, which will allow us to concentrate the dose to a dry powder for aerosol delivery, in accordance with the present disclosure. The proposed experimental setup would use the required epinephrine dosage (e.g., 10 mg+ or 20 mg+) be dissolved in ≤1.0 cc of water, so as to form a "dry" powder. The required epinephrine will be delivered within the time required for 2-4 breaths from an Ambu bag during CPR.

Drug preparation for dry powder delivery requires that we grind/mill the epinephrine into small crystals. Such milling to the target particle size range of less than about 10 microns, such as between 2 µm and 5 µm, can be by any appropriate method. For example, epinephrine can be placed between 2 standard microscopic glass slides and ground. The use of this technique in combination with a cell counter, will allow us to verify that our samples are consistently in the target particle range of about 2-5 microns.

Example 3

Proposed Future Experiments

These experiments are organized into two series, each of which addresses one of the present experimental aims. Animal preparation will be the same for both series. All experiments will be performed on anesthetized pigs subjected to 6-minutes of untreated ventricular fibrillation (VF); thereafter, a series of similar protocols will be performed, but using different devices.

The first series of experiments (Series 1) will be carried out to determine the pharmacokinetics and effectiveness of the currently disclosed dry powder ET system's delivery of epinephrine (or other suitable therapeutic agents, such as other $\beta_2$-agonists) versus central IV or ET delivery following CPR during ventricular fibrillation (VF). This series will include 4 groups of 6 animals, for a total of 24 experiments.

In the first series of experiments we will inject 10 ml of KCl to induce VF. The uninterrupted VF period will last for 6 min followed by 2 min of CPR. We do not anticipate animals returning to spontaneous circulation. Rather, the objective is to evaluate the appearance time, time to peak concentration and the area under the curve (AUC) of the arterial concentrations of epinephrine over time after ET dry powder administration. Particles between 2-5 microns may enhance drug delivery and absorption. Therefore, we will determine the most effective dose using 0.2 mg/kg (the standard IV dose) or 0.4 mg/kg (SOC endotracheal dose). After 2 min of CPR epinephrine will be delivered via the endotracheal route followed by 2 breaths. Central venous and SOC ET doses of epinephrine will follow standardized dosing for swine of 0.2 mg/kg and 0.4 mg/kg respectively. The endotracheal dose has been established at 2× the standard IV dose of 0.2 mg/kg. CPR will be continued for 8 min post drug delivery. We will sample arterial (aortic) blood at time points BL, VF 180 s, 0, 15, 30, 60, 120, 180, 240, 360, and 480 s of CPR. CPR will be standardized in all groups as we did in our preliminary studies by the use of an oxygen-driven mechanical resuscitation device (e.g., the THUMPER®, available from Michigan Instruments, Grand Rapids, Mich.). The device delivers chest compressions and provides ventilation with 100% oxygen. Chest compressions will be done in the anterior/posterior position, at a depth of 2 inches, a rate of 80 compressions per minute, and a 50% duty cycle. Ventilation will not be delivered. Blood samples will be placed in pre chilled tubes containing the preservative sodium metabisulfite and kept on ice. Blood samples will be spun in a refrigerated centrifuge and plasma will be stored at −80° C. for HPLC analysis at a latter date.

The effect that the dose and route of epinephrine delivery have on MAP, ETCO$_2$, CO, CPP, LV end diastolic pressure, pulse, and heart rate will be compared, and these results will also be compared to the results from those in series 2, discussed below.

In order to determine the pharmacokinetics and effectiveness of a novel aerosol ET system's delivery of epinephrine versus, standard of care ET and central vein during CPR of VF, as a second series of experiments (Series 2) will be performed, using 4 groups of 6 swine, for a total of 24 experiments, as set out as follows:

1. Dry powder 0.2 mg/kg, epinephrine n=6
2. Dry powder 0.4 mg/kg epinephrine, n=6
3. IV central 0.2 mg/kg epinephrine n=6
4. Standard ET 0.4 mg/kg epinephrine n=6

The protocol for Series 2 will remain the exactly the same as Series 1 described previously, with the exception that the aerosol device described in the present disclosure will be used. Briefly, VF will be untreated and allowed to persist for 6 minutes before experimental interventions begin. There will be 2 min of CPR delivered before drugs are delivered followed by an additional 8 min of CPR w/o ventilation. We will sample arterial (aortic) blood at time points BL, VF 180 s, 0, 15, 30, 60, 120, 180, 240, 360, and 480 s of CPR. CPR will be standardized in all groups as we did in our preliminary studies by the use of an oxygen-driven mechanical resuscitation device (e.g., the THUMPER®, available from Michigan Instruments, Grand Rapids, Mich.). Ventilation will not be delivered. Blood samples will be placed in pre chilled tubes containing the preservative sodium metabisulfite and kept on ice. Blood samples will be spun in a refrigerated centrifuge and plasma will be stored at −80° C. for HPLC analysis at a later date.

We will also compare the effect that the dose and route of epinephrine delivery have on MAP, ETCO$_2$, CO, CPP, LV end diastolic pressure, pulse, and heart rate. We will compare results from the following groups, and thereafter compare the results. Groups to be studied include:

1 ET aerosolized epinephrine 0.2 mg/kg, n=6
2. ET aerosolized epinephrine 0.4 mg/kg, n=6
3. IV central 0.2 mg/kg epinephrine, n=6
4. Standard ET 0.4 mg/kg epinephrine, n=6

The invention has been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intends to protect all such modifications and improvements to the full extent that such falls within the scope or range of equivalent of the following claims.

What is claimed is:

1. A single unit dosage form for pulmonary delivery of an adrenergic agonist, comprising a single unit dosage receptacle containing a single delivery dosage amount of at least 20 mg of the adrenergic agonist as an essentially solvent free powder milled to an average particle size of less than about 10 μm, and a pharmaceutically acceptable single dose quantity of a non-CFC haloalkane propellant.

2. The single unit dosage form of claim 1, wherein the haloalkane propellant is 1,1,2,2-tetrafluroethane (R-134a).

3. The single unit dosage form of claim 1, wherein the adrenergic agonist is selected from the group consisting of epinephrine, norepinephrine, α-methylnorepinephrine, isoproterenol, albuterol, isoetharine, metaproterenol, terbutaline, pseudoephedrine, phenylephrine, and ephedrine, epinephrine analogs, and pharmaceutically acceptable salts, solvates, hydrates, prodrugs, and polymorphs thereof.

4. The single unit dosage form of claim 1, wherein the at least one adrenergic agonist is milled to an average particle size of less than about 5 μm.

5. The single unit dosage form of claim 1, wherein the single unit dosage receptacle further comprises one or more additional therapeutic agents selected from the group consisting of nerve-agent therapeutic agents, steroids, anticholinesterases, antioxidants, β$_2$ agonists, anti-inflammatories, NSAIDs, bacterial protein synthesis inhibitors, interferons, oxazolidinones, epinephrine, combinations thereof, as well as pharmaceutically-acceptable salts, prodrugs, polymorphs, and solvates thereof.

6. The single unit dosage form for pulmonary delivery of claim 1, wherein the adrenergic agonist is selected from the group consisting of epinephrine, norepinephrine, α-methylnorepinephrine, isoproterenol, albuterol, aminophylline, beclomethasone, dyphylline, flunisolide, isoetharine, metaproterenol, oxtriphylline, terbutaline, theophylline, pseudoephedrine, phenylephrine, and ephedrine, alone or in combination, as well as the pharmaceutically-acceptable salts, solvates, hydrates, prodrugs, and polymorphs thereof.

7. A method for aerosolizing a bioactive adrenergic agonist composition, the method comprising:
providing an aerosol delivery system that comprises at least two separate chambers separated by a valve, one propellant chamber comprising a pharmaceutically acceptable single dose quantity of propellant and a second active agent chamber comprising an essentially solvent free dry powder drug composition that includes an adrenergic agonist, wherein the system is adapted and dimensioned to admix and deliver at least 20 mg of the adrenergic agonist in one emergency treatment when the valve separating the chambers is opened and the propellant mixes with the drug composition and forms an aerosol for inhalation by a patient upon release from the system.

8. The method of claim 7, wherein the the active agent chamber further comprises one or more additional therapeutic agents selected from the group consisting of nerve-agent therapeutic agents, steroids, anticholinesterases, antioxidants, β$_2$ agonists, anti-inflammatories, NSAIDs, bacterial protein synthesis inhibitors, interferons, oxazolidinones, epinephrine, combinations thereof, as well as pharmaceutically-acceptable salts, prodrugs, polymorphs, and solvates thereof.

9. The method of claim 7, wherein the essentially solvent free dry powder drug composition consists essentially of epinephrine or a salt thereof in a dosage amount of at least 20 mg.

10. The method of claim 7, wherein the adrenergic agonist is selected from the group consisting of epinephrine, norepinephrine, α-methylnorepinephrine, isoproterenol, albuterol, aminophylline, beclomethasone, dyphylline, flunisolide, isoetharine, metaproterenol, oxtriphylline, terbutaline, theophylline, pseudoephedrine, phenylephrine, and ephedrine, alone or in combination, as well as the pharmaceutically-acceptable salts, solvates, hydrates, prodrugs, and polymorphs thereof.

* * * * *

UNITED STATES PATENT AND TRADEMARK OFFICE
CERTIFICATE OF CORRECTION

| | | |
|---|---|---|
| PATENT NO. | : 8,597,616 B2 | Page 1 of 1 |
| APPLICATION NO. | : 12/256438 | |
| DATED | : December 3, 2013 | |
| INVENTOR(S) | : Kraft et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1136 days.

Signed and Sealed this
Fourteenth Day of April, 2015

Michelle K. Lee
*Director of the United States Patent and Trademark Office*